United States Patent
Ragini et al.

(10) Patent No.: US 7,687,626 B2
(45) Date of Patent: Mar. 30, 2010

(54) ORGANOMETALLIC COMPLEX AND ORGANIC ELECTROLUMINESCENT DEVICE USING THE SAME

(75) Inventors: Das Rupasree Ragini, Yongin-si (KR); Hee-kyung Kim, Yongin-si (KR); O-hyun Kwon, Yongin-si (KR); Young-hun Byun, Yongin-si (KR); Joon-yong Park, Yongin-si (KR); Jung-bae Song, Yongin-si (KR); Eun-sil Han, Yongin-si (KR)

(73) Assignee: Samsung Electronics Co., Ltd. (KR)

( * ) Notice: Subject to any disclaimer, the term of this patent is extended or adjusted under 35 U.S.C. 154(b) by 81 days.

(21) Appl. No.: 11/932,121

(22) Filed: Oct. 31, 2007

(65) Prior Publication Data

US 2008/0103308 A1  May 1, 2008

(30) Foreign Application Priority Data

Oct. 31, 2006  (KR)  ...................... 10-2006-0106725

(51) Int. Cl.
 *C07F 15/00* (2006.01)
 *H01L 51/50* (2006.01)
(52) U.S. Cl. ........................... 546/10; 428/690; 428/917
(58) Field of Classification Search .................. 546/10, 546/2; 428/690, 917
 See application file for complete search history.

(56) References Cited

U.S. PATENT DOCUMENTS 7,501,188 B2 *  3/2009  Son et al. ..................... 428/690

OTHER PUBLICATIONS

Garces, F.O., et al.; "Synthesis, Structure, Electrochemistry, and Photophysics of Methyl-Substituted Phenylpyridine Ortho-Metalated Iridium(III) Complexes"; Inorg. Chem.; vol. 27; pp. 3464-3471; 1988.

Baldo, M.A., et al.; "Highly efficient phosphorescent emission from organic electroluminescent devices"; Nature; vol. 395; pp. 151-154; Sep. 1998.

Baldo, M.A., et al; "Excitonic singlet-triplet ratio in a semiconducting organic thin film"; Physical Review B; vol. 60, No. 20; pp. 14422-14428; Nov. 15, 1999.

* cited by examiner

*Primary Examiner*—Charanjit S Aulakh
(74) *Attorney, Agent, or Firm*—Cantor Colburn LLP

(57) ABSTRACT

Provided are a highly efficient phosphorescent organometallic complex and an organic electroluminescent (EL) device using the same. The organometallic complex can be used in the formation of an organic layer of the organic EL device, and can emit light in a red wavelength range as a highly efficient phosphorescent material. The organic EL device using the organometallic complex can exhibit high brightness and a low driving voltage.

8 Claims, 7 Drawing Sheets

ORGANOMETALLIC COMPLEX AND ORGANIC ELECTROLUMINESCENT DEVICE USING THE SAME

CROSS-REFERENCE TO RELATED PATENT APPLICATION

This application claims priority from Korean Patent Application No. 10-2006-0106725, filed on Oct. 31, 2006, in the Korean Intellectual Property Office, the disclosure of which is incorporated herein in its entirety by reference.

BACKGROUND OF THE INVENTION

1. Field of the Invention

The present invention relates to an organometallic complex and an organic electroluminescent device using the same. More particularly, the present invention relates to an organometallic complex capable of emitting light in a red wavelength range, and an organic electroluminescent device using the organometallic complex as an organic layer forming material.

2. Description of the Related Art

Organic electroluminescent (EL) devices are active emission display devices that emit light by recombination of electrons and holes in a thin layer (hereinafter, referred to as "organic layer") formed of a fluorescent or phosphorescent organic compound when a current is applied to the organic layer. Organic EL devices have advantages such as lightness, simple constitutional elements, easy fabrication process, superior image quality, and wide viewing angles. In addition, the organic EL devices can achieve high color purity and perfectly create dynamic images, and have electrical properties suitable for use in portable electronic equipment due to low power consumption and low driving voltages.

Generally, organic EL devices have a sequentially stacked structure of an anode, a hole transport layer, an emitting layer, an electron transport layer, and a cathode on a substrate. Here, the hole transport layer, the emitting layer, and the electron transport layer are organic layers formed of organic compounds. Organic EL devices having the above-described structure are operated as follows. When voltages are applied to an anode and a cathode, holes from the anode are moved to an emitting layer via a hole transport layer. On the other hand, electrons from the cathode are moved to the emitting layer via an electron transport layer. In the emitting layer, the carriers are recombined to generate excitons. By the radiative decay of the excitons, light emission occurs at the wavelength corresponding to the bandgap of a material.

Materials that can be used to form an emitting layer in an organic EL device are divided into fluorescent materials using a singlet exciton and phosphorescent materials using a triplet exciton according to emission mechanisms. The emitting layer is formed of a fluorescent or phosphorescent material alone or an appropriate host material doped with the fluorescent or phosphorescent material. Singlet excitons and triplet excitons are formed in the host during electronic excitation. At this time, a statistical ratio of the singlet excitons to the triplet excitons is 1 to 3 [Baldo, et al., Phys. Rev. B, 1999, 60, 14422].

An organic EL device including an emitting layer formed of a fluorescent material has a disadvantage in that triplet excitons formed in the host are wasted. On the other hand, an organic EL device including an emitting layer formed of a phosphorescent material has an advantage of 100% internal quantum efficiency since both singlet excitons and triplet excitons can be utilized [Baldo, et al., Nature, Vol. 395, 151-154, 1998]. In this respect, an emitting layer formed of a phosphorescent material can achieve significantly high emission efficiency, relative to an emitting layer formed of a fluorescent material.

When a heavy metal such as Ir, Pt, Rh, and Pd is introduced into an organic molecule, the heavy atom effect leads to spin-orbital coupling, whereby a triplet state and a singlet state are mixed. Therefore, a forbidden transition is induced, which allows efficient phosphorescent emission even at room temperature.

As a high-efficient phosphorescent material, there have been reported various materials based on transition metal compounds containing transition metals such as iridium and platinum. However, phosphorescent materials suitable for highly efficient full color display devices are still being required.

SUMMARY OF THE INVENTION

The present invention provides an organometallic complex capable of efficiently emitting light.

The present invention also provides an organic electroluminescent (EL) device using the organometallic complex.

According to an aspect of the present invention, there is provided an organometallic complex represented by Formula 1 below:

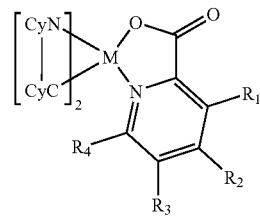

<Formula 1> wherein,

M is Ir, Os, Pt, Pb, Re, Ru, or Pd;

CyN is a substituted or unsubstituted C3-C60 heterocyclic group including nitrogen bound to M or a substituted or unsubstituted C3-C60 heteroaryl group including nitrogen bound to M;

CyC is a substituted or unsubstituted C4-C60 carbocyclic group including carbon bound to M, a substituted or unsubstituted C3-C60 heterocyclic group including carbon bound to M, a substituted or unsubstituted C6-C60 aryl group including carbon bound to M, or a substituted or unsubstituted C3-C60 heteroaryl group including carbon bound to M;

CyN-CyC is a cyclometalating ligand bound to M via nitrogen (N) and carbon (C); and $R_1$, $R_2$, $R_3$, and $R_4$ are each independently hydrogen, a hydroxyl group, a sulfo group, a halogen atom, a carboxyl group, an amino group, a nitro group, a cyano group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_1$-$C_{20}$ heteroalkyl group, a substituted or unsubstituted $C_6$-$C_{30}$ aryl group, a substituted or unsubstituted $C_6$-$C_{30}$ aryloxy group, a substituted or unsubstituted $C_2$-$C_{20}$ alkoxycarbonyl group, a substituted or unsubstituted $C_1$-$C_{20}$ acyloxy group, a substituted or unsubstituted $C_1$-$C_{20}$ acylamino group, a substituted or unsubstituted $C_2$-$C_{20}$ alkoxycarbonylamino group, a substituted or unsubstituted $C_7$-$C_{30}$ aryloxycarbonylamino group, a sulfonylamino group, a sulfamoyl group, a carbamoyl group, a substituted or unsubstituted $C_6$-$C_{30}$ arylthio group, a substituted or unsubstituted $C_3$-$C_{30}$ heteroarylthio group, a sulfonyl group, a sulfinyl group, an ureido group, a phosphoric acid amido group, a hydroxaminic group, a sulfino group, a hydrazine group, an imino group, a silyl group, a phosphino group, a substituted or unsubstituted $C_4$-$C_{30}$ cycloalkyl group, a substituted or unsubstituted $C_7$-$C_{30}$ arylalkyl group, a substituted or unsubstituted $C_5$-$C_{30}$ heteroaryl group, or a substituted or unsubstituted $C_3$-$C_{30}$ heteroarylalkyl group, and two or more of $R_1$, $R_2$, $R_3$, and $R_4$ are fused to form a bicyclic, tricyclic, tetracyclic, or pentacyclic fused ring of 5, 6, or 7-membered ring.

According to an embodiment of the present invention, the compound of Formula 1 may be a compound represented by Formula 2 below:

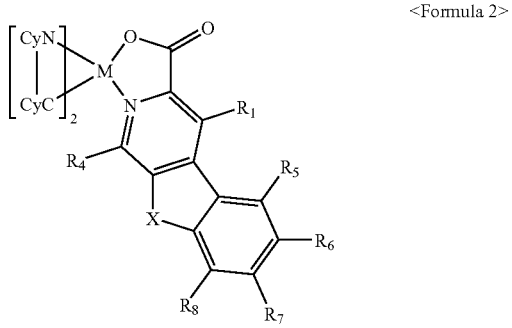

<Formula 2> wherein,

M, CyN, and CyC are as defined above;

X is $NR_a$, O, S, $SiR_bR_c$ or $CR_dR_e$;

$R_1$, $R_4$, $R_5$, $R_6$, $R_7$, $R_9$, $R_a$, $R_b$, $R_c$, $R_d$, and $R_e$ are each independently hydrogen, a hydroxyl group, a sulfo group, a halogen atom, a carboxyl group, an amino group, a nitro group, a cyano group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_1$-$C_{20}$ heteroalkyl group, a substituted or unsubstituted $C_6$-$C_{30}$ aryl group, a substituted or unsubstituted $C_6$-$C_{30}$ aryloxy group, a substituted or unsubstituted $C_2$-$C_{20}$ alkoxycarbonyl group, a substituted or unsubstituted $C_1$-$C_{20}$ acyloxy group, a substituted or unsubstituted $C_1$-$C_{20}$ acylamino group, a substituted or unsubstituted C2-C20 alkoxycarbonylamino group, a substituted or unsubstituted $C_7$-$C_{30}$ aryloxycarbonylamino group, a sulfonylamino group, a sulfamoyl group, a carbamoyl group, a substituted or unsubstituted $C_6$-$C_{30}$ arylthio group, a substituted or unsubstituted C3-C30 heteroarylthio group, a sulfonyl group, a sulfinyl group, an ureido group, a phosphoric acid amido group, a hydroxaminic group, a sulfino group, a hydrazine group, an imino group, a silyl group, a phosphino group, a phosphinyl a substituted or unsubstituted C4-C30 cycloalkyl group, a substituted or unsubstituted $C_7$-$C_{30}$ arylalkyl group, a substituted or unsubstituted $C_5$-$C_{30}$ heteroaryl group, or a substituted or unsubstituted $C_3$-$C_{30}$ heteroarylalkyl group, and two or more of $R_1$, $R_4$, $R_5$, $R_6$, $R_7$, $R_8$, and $R_9$ may be fused to form a 5, 6, or 7-membered fused ring.

According to another aspect of the present invention, there is provided an organic EL device including an organic layer between a pair of electrodes, the organic layer including the above-described organometallic complex.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1A:
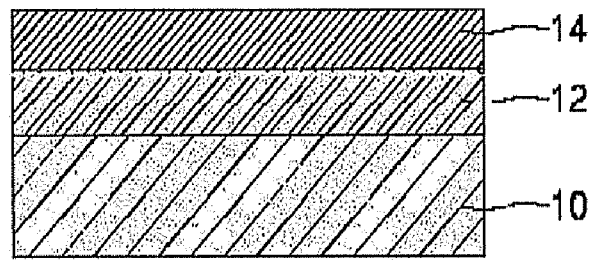
FIGS. 1A through 1F are schematic views illustrating organic electroluminescent (EL) devices according to embodiments of the present invention.

The present invention will now be described in more detail.

The present invention provides an organometallic complex having a new auxiliary ligand introduced therein, as represented by Formula 1 below. The organometallic complex can produce sufficient RGB emission in a triplet metal-to-ligand charge-transfer (MLCT) state. In particular, the organometallic complex is a thermally stable, highly efficient phosphorescent material that emits light in a wavelength range of 400 to 700 nm, and thus, can provide RGB or white light in the field of organic electroluminescent (EL) devices, etc.

<Formula 1> wherein,

M is Ir, Os, Pt, Pb, Re, Ru, or Pd;

CyN is a substituted or unsubstituted C3-C60 heterocyclic group including nitrogen bound to M or a substituted or unsubstituted C3-C60 heteroaryl group including nitrogen bound to M;

CyC is a substituted or unsubstituted C4-C60 carbocyclic group including carbon bound to M, a substituted or unsubstituted C3-C60 heterocyclic group including carbon bound to M, a substituted or unsubstituted C6-C60 aryl group including carbon bound to M, or a substituted or unsubstituted C3-C60 heteroaryl group including carbon bound to M;

CyN-CyC is a cyclometalating ligand bound to M via nitrogen (N) and carbon (C); and $R_1$, $R_2$, $R_3$, and $R_4$ are each independently hydrogen, a hydroxyl group, a sulfo group, a halogen atom, a carboxyl group, an amino group, a nitro group, a cyano group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_1$-$C_{20}$ heteroalkyl group, a substituted or unsubstituted $C_6$-$C_{30}$ aryl group, a substituted or unsubstituted $C_6$-$C_{30}$ aryloxy group, a substituted or unsubstituted $C_2$-$C_{20}$ alkoxycarbonyl group, a substituted or unsubstituted $C_1$-$C_{20}$ acyloxy group, a substituted or unsubstituted $C_1$-$C_{20}$ acylamino group, a substituted or unsubstituted C2-C20 alkoxycarbonylamino group, a substituted or unsubstituted $C_7$-$C_{30}$ aryloxycarbonylamino group, a sulfonylamino group, a sulfamoyl group, a carbamoyl group, a substituted or unsubstituted $C_6$-$C_{30}$ arylthio group, a substituted or unsubstituted C3-C30 heteroarylthio group, a sulfonyl group, a sulfinyl group, an ureido group, a phosphoric acid amido group, a hydroxaminic group, a sulfino group, a hydrazine group, an imino group, a silyl group, a phosphino group, a substituted or unsubstituted C4-C30 cycloalkyl group, a substituted or unsubstituted $C_7$-$C_{30}$ arylalkyl group, a substituted or unsubstituted $C_5$-$C_{30}$ heteroaryl group, or a substituted or unsubstituted $C_3$-$C_{30}$ heteroarylalkyl group, and two or more of $R_1$, $R_2$, $R_3$, and $R_4$ are fused to form a bicyclic, tricyclic, tetracyclic, or pentacyclic fused ring of 5, 6, or 7-membered rings.

In the organometallic complex of Formula 1, M is a central metal binding with a cyclometallating ligand and/or an auxiliary ligand. For example, M is Ir, Os, Pt, Pb, Re, Ru, or Pd, preferably Ir or Pt, but is not limited thereto.

In Formula 1, CyN is a heterocyclic or heteroaryl group including nitrogen directly coordinating with the central metal M. The heterocyclic ring is a substituted or unsubstituted C3-C60 heterocyclic ring including a heteroatom such as N, O, S, and/or P as a main element forming the ring. Examples of the heterocyclic ring include, but are not limited to, pyrrolidine, morpholine, thiomorpholine, thiazolidine, etc. The heteroaryl group is a substituted or unsubstituted C3-C60 heteroaryl group including a heteroatom such as N, O, S, and/or P as a main element forming the ring. Examples of the heteroaryl group include, but are not limited to, pyridine, 4-methoxypyridine, quinoline, pyrrole, indole, pyrazine, pyrazole, imidazole, pyrimidine, quinazoline, thiazole, oxazole, triazine, 1,2,4-triazole, etc.

With respect to CyC of Formula 1, the substituted or unsubstituted C4-C60 carbocyclic group including carbon bound to M may be cyclohexane, cycloheptane, etc., the substituted or unsubstituted C3-C60 heterocyclic group including carbon bound to M may be tetrahydrofuran, 1,3-dioxane, 1,3-dithiane, 1,3-dithiolane, 1,4-dioxa-8-azaspiro[4,5]decane, 1,4-dioxaspiro[4,5]decan-2-one, etc., the substituted or unsubstituted C6-C60 aryl group including carbon bound to M may be phenyl, 1,3-benzodioxole, biphenyl, terphenyl, naphthalene. anthracene, azulene, etc., and the substituted or unsubstituted C3-C60 heteroaryl group including carbon bound to M may be thiophene, furan2(5H)-furanone, pyridine, coumarin, imidazole, 2-phenylpyridine, 2-benzothiazole, 2-benzoxazole, 1-phenylpyrazole, 1-naphthylpyrazole, 5-(4-methoxyphenyl)pyrazole, 2,5-bisphenyl-1,3,4-oxadiazole, 2,3-benzofuran-2-(4-biphenyl)-6-phenyl benzoxazole, etc. At least one hydrogen atom present in these groups may be substituted by a straight or branched C1-C10 alkoxy group, a cyano group, a halogen atom, etc.

In Formula 1, respective substituents of CyN-CyC may be connected to form a substituted or unsubstituted 4, 5, 6, or 7-membered cyclic group or a substituted or unsubstituted 4, 5, 6, or 7-membered heterocyclic group, in particular, a condensed 4, 5, 6, or 7-membered cyclic or heterocyclic group. Here, the cyclic or heterocyclic group is a C1-C30 cycloalkyl group, a C1-C30 heterocycloalkyl group, a C6-C30 aryl group, or a C4-C30 heteroaryl group, and may be substituted by at least one substituent. The term "hetero" used herein has the meaning of a heteroatom such as N, O, P, or S.

In the compound of Formula 1, at least one hydrogen may be substituted by any of various substituents, such as a halogen atom, —$OR_1$, —$N(R_1)_2$, —$P(R_1)_2$, —$POR_1$, —$PO_2R_1$, —$PO_3R_1$, —$SR_1$, —$Si(R_1)_3$, —$B(R_1)_2$, —$B(OR_1)_2$, —C(O)$R_1$, —C(O)$OR_1$, —C(O)N($R_1$), —CN, —$NO_2$, —$SO_2$, —$SOR_1$, —$SO_2R_1$, and —$SO_3R_1$ where $R_1$ is selected from hydrogen, a halogen atom, a substituted or unsubstituted $C_1$-$C_{20}$ alkyl group, a substituted or unsubstituted $C_1$-$C_{10}$ alkoxy group, a substituted or unsubstituted $C_2$-$C_{20}$ alkenyl group, a substituted or unsubstituted $C_2$-$C_{20}$ alkynyl group, a substituted or unsubstituted $C_1$-$C_{20}$ heteroalkyl group, a substituted or unsubstituted $C_6$-$C_{40}$ aryl group, a substituted or unsubstituted $C_7$-$C_{40}$ arylalkyl group, a substituted or unsubstituted $C_7$-$C_{40}$ alkylaryl group, a substituted or unsubstituted $C_2$-$C_{40}$ heteroaryl group, and a substituted or unsubstituted $C_3$-$C_{40}$ heteroarylalkyl group.

The cyclometallating ligand CyN-CyC may be represented by any of the following formulae, but is not limited thereto:

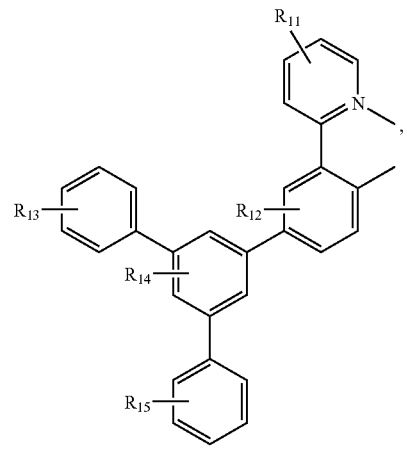

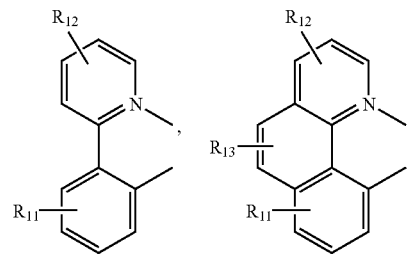

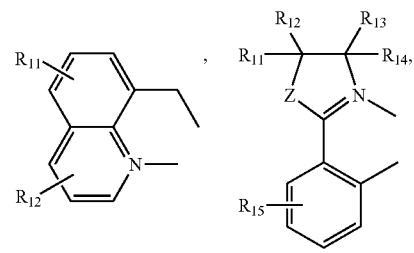

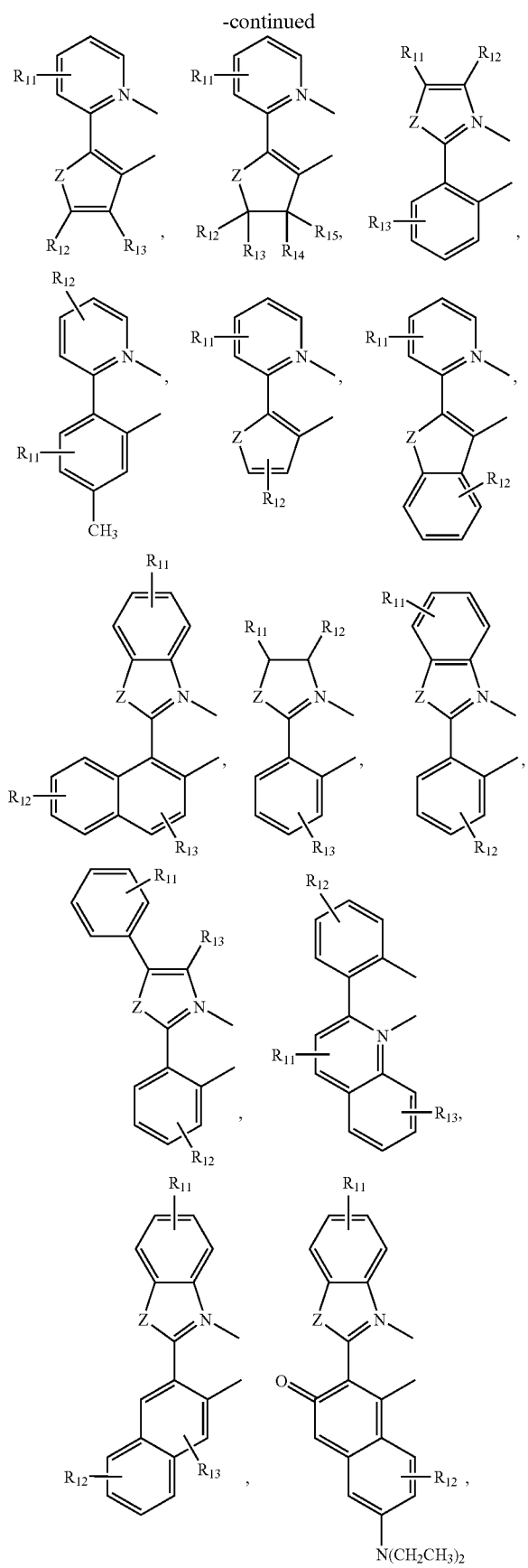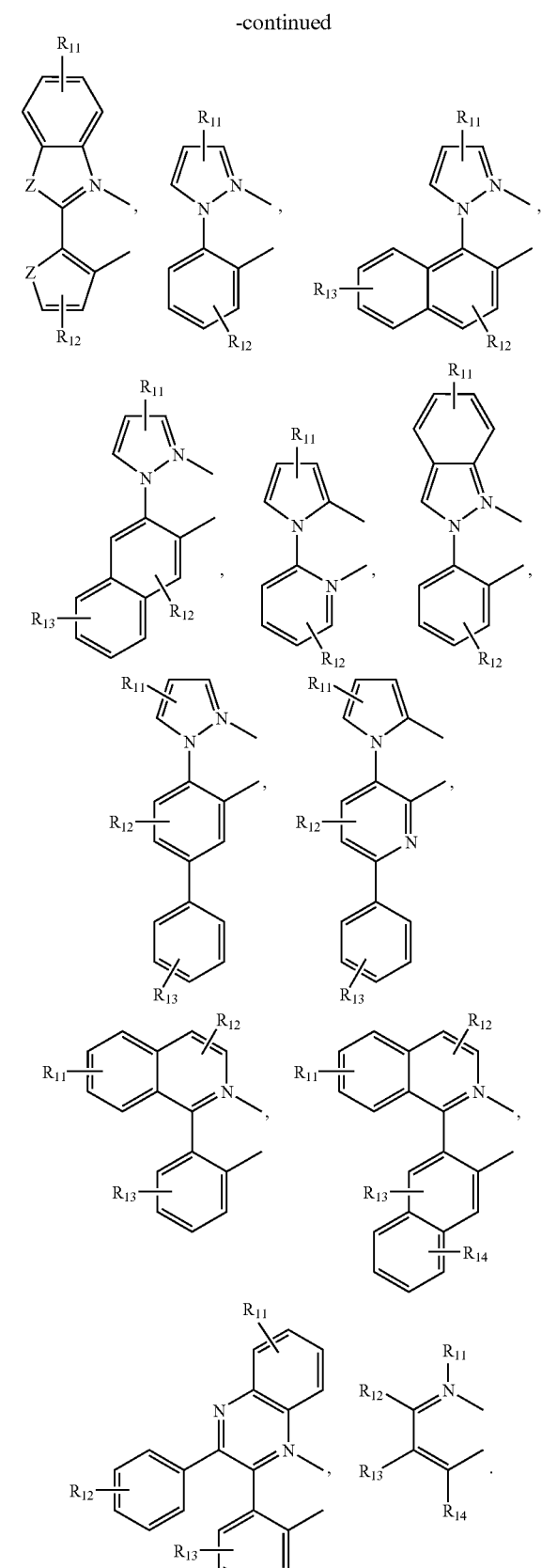

wherein, $R_{11}, R_{12}, R_{13}, R_{14},$ and $R_{15}$ are each independently a mono-substituted or polysubstituted functional group selected from hydrogen, a halogen atom, —OR, —N(R)$_2$, —P(R)$_2$, —POR, —PO$_2$R, —PO$_3$R, —SR, —Si(R)$_3$, —B(R)$_2$, —B(OR)$_2$, —C(O)R, —C(O)OR, —C(O)N(R), —CN, —NO$_2$, —SO$_2$, —SOR, —SO$_2$R, —SO$_3$R, a C$_1$-C$_{20}$ alkyl group, and a C$_6$-C$_{20}$ aryl group where R is selected from hydrogen, a halogen atom, a substituted or unsubstituted C$_1$-C$_{20}$ alkyl group, a substituted or unsubstituted C$_1$-C$_{10}$ alkoxy group, a substituted or unsubstituted C$_2$-C$_{20}$ alkenyl group, a substituted or unsubstituted C$_2$-C$_{20}$ alkynyl group, a substituted or unsubstituted C$_1$-C$_{20}$ heteroalkyl group, a substituted or unsubstituted C$_6$-C$_{40}$ aryl group, a substituted or unsubstituted C$_7$-C$_{40}$ arylalkyl group, a substituted or unsubstituted C$_7$-C$_{40}$ alkylaryl group, a substituted or unsubstituted C$_2$-C$_{40}$ heteroaryl group, and a substituted or unsubstituted C$_3$-C$_{40}$ heteroarylalkyl group; and Z is S, O, or NR$_0$ where R$_0$ is hydrogen or a C1-C20 alkyl group.

In the organometallic complex of Formula 1, an auxiliary ligand capable of bound to the central metal includes the following examples:

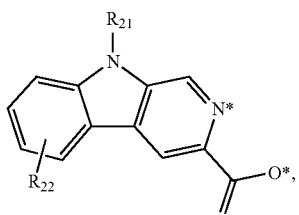

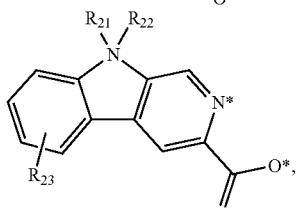

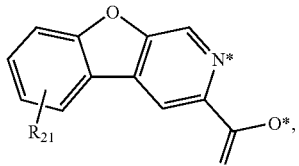

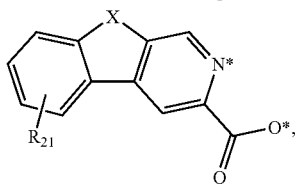

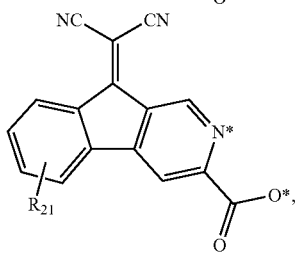

-continued

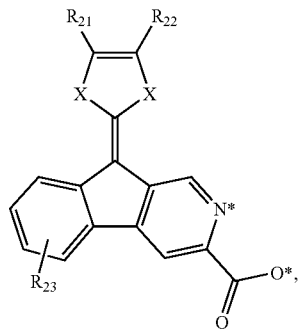

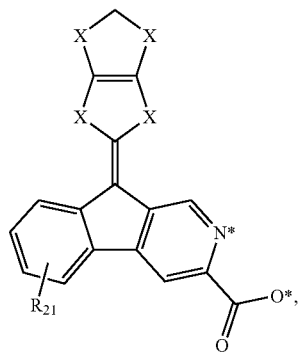

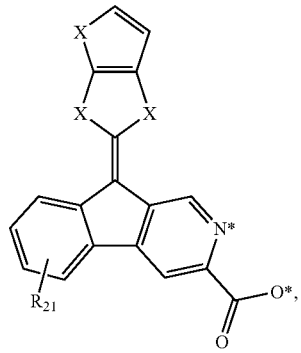

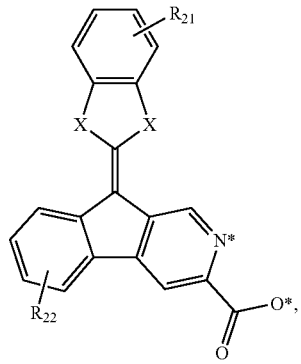

-continued

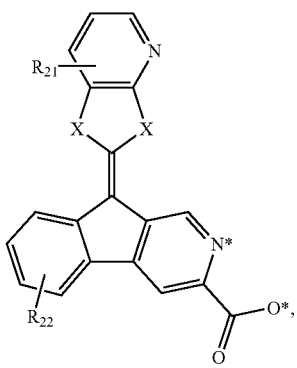

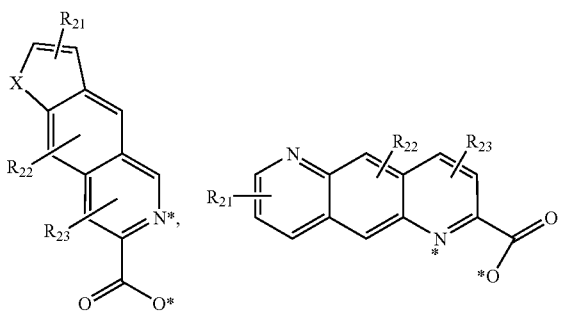

wherein $R_{21}$, $R_{22}$, and $R_{23}$ are each independently a mono-substituted or polysubstituted functional group selected from hydrogen, a halogen atom, —OR, —N(R)$_2$, —P(R)$_2$, —POR, —PO$_2$R, —PO$_3$R, —SR, —Si(R)$_3$, —B(R)$_2$, —B(OR)$_2$, —C(O)R, —C(O)OR, —C(O)N(R), —CN, —NO$_2$, —SO$_2$, —SOR, —SO$_2$R, —SO$_3$R, a $C_1$-$C_{20}$ alkyl group, and a $C_6$-$C_{20}$ aryl group where R is selected from hydrogen, a halogen atom, a substituted or unsubstituted $C_1$-$C_{20}$ alkyl group, a substituted or unsubstituted $C_1$-$C_{10}$ alkoxy group, a substituted or unsubstituted $C_2$-$C_{20}$ alkenyl group, a substituted or unsubstituted $C_2$-$C_{20}$ alkynyl group, a substituted or unsubstituted $C_1$-$C_{20}$ heteroalkyl group, a substituted or unsubstituted $C_6$-$C_{40}$ aryl group, a substituted or unsubstituted $C_7$-$C_{40}$ arylalkyl group, a substituted or unsubstituted $C_7$-$C_{40}$ alkylaryl group, a substituted or unsubstituted $C_2$-$C_{40}$ heteroaryl group, and a substituted or unsubstituted $C_3$-$C_{40}$ heteroarylalkyl group; and X is oxygen or sulfur.

The organometallic complex of Formula 1 may be a compound represented by Formula 2 below:

<Formula 2> wherein,

M, CyN, and CyC are as defined above;

X is $NR_a$, O, S, $SiR_bR_c$ or $CR_dR_e$;

$R_1$, $R_4$, $R_5$, $R_6$, $R_7$, $R_8$, $R_a$, $R_b$, $R_c$, $R_d$, and $R_e$ are each independently hydrogen, a hydroxyl group, a sulfo group, a halogen atom, a carboxyl group, an amino group, a nitro group, a cyano group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_1$-$C_{20}$ heteroalkyl group, a substituted or unsubstituted $C_6$-$C_{30}$ aryl group, a substituted or unsubstituted $C_6$-$C_{30}$ aryloxy group, a substituted or unsubstituted $C_2$-$C_{20}$ alkoxycarbonyl group, a substituted or unsubstituted $C_1$-$C_{20}$ acyloxy group, a substituted or unsubstituted $C_1$-$C_{20}$ acylamino group, a substituted or unsubstituted C2-C20 alkoxycarbonylamino group, a substituted or unsubstituted $C_7$-$C_{30}$ aryloxycarbonylamino group, a sulfonylamino group, a sulfamoyl group, a carbamoyl group, a substituted or unsubstituted $C_6$-$C_{30}$ arylthio group, a substituted or unsubstituted C3-C30 heteroarylthio group, a sulfonyl group, a sulfinyl group, an ureido group, a phosphoric acid amido group, a hydroxaminic group, a sulfino group, a hydrazine group, an imino group, a silyl group, a phosphino group, a phosphinyl a substituted or unsubstituted C4-C30 cycloalkyl group, a substituted or unsubstituted $C_7$-$C_{30}$ arylalkyl group, a substituted or unsubstituted $C_5$-$C_{30}$ heteroaryl group, or a substituted or unsubstituted $C_3$-$C_{30}$ heteroarylalkyl group, and two or more of $R_1$, $R_4$, $R_5$, $R_6$, $R_7$, $R_8$, and $R_9$ may be fused to form a 5, 6, or 7-membered fused ring.

The compound of Formula 2 may be selected from compounds represented by Formulae 4 through 9 below:

<Formula 4>
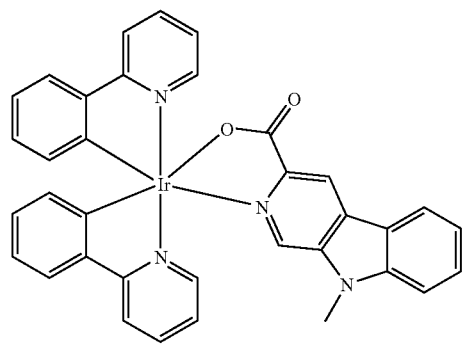
<Formula 5>
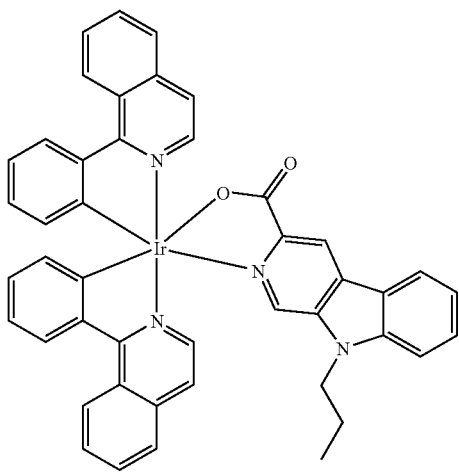
<Formula 6>
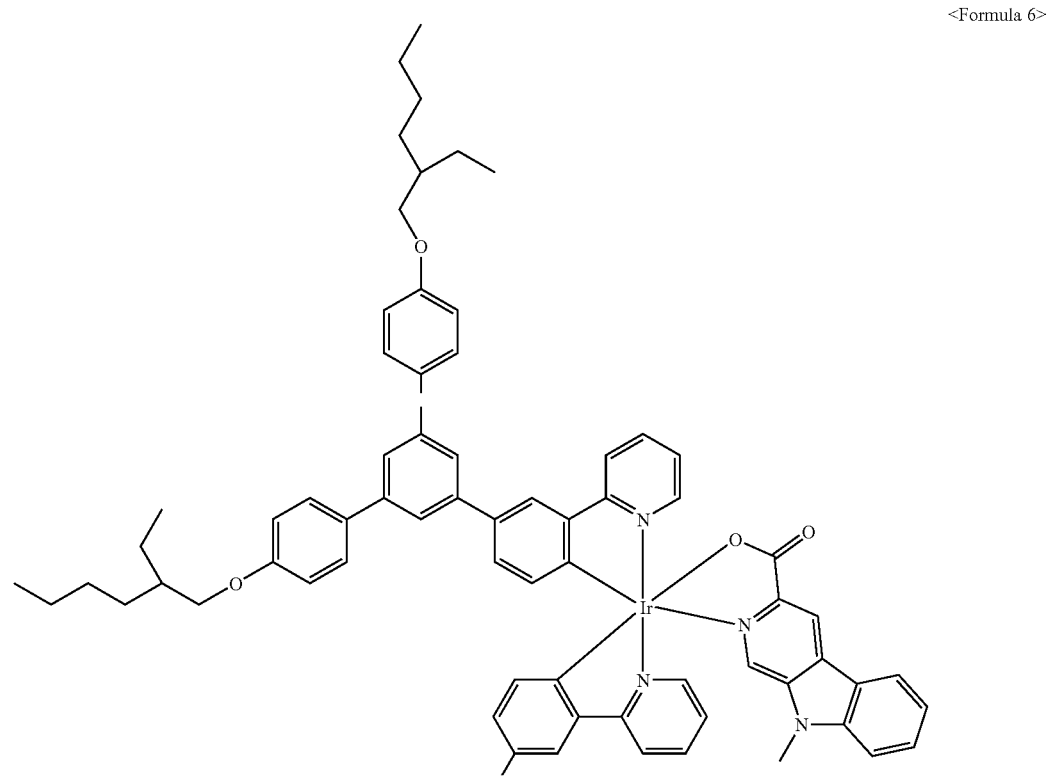

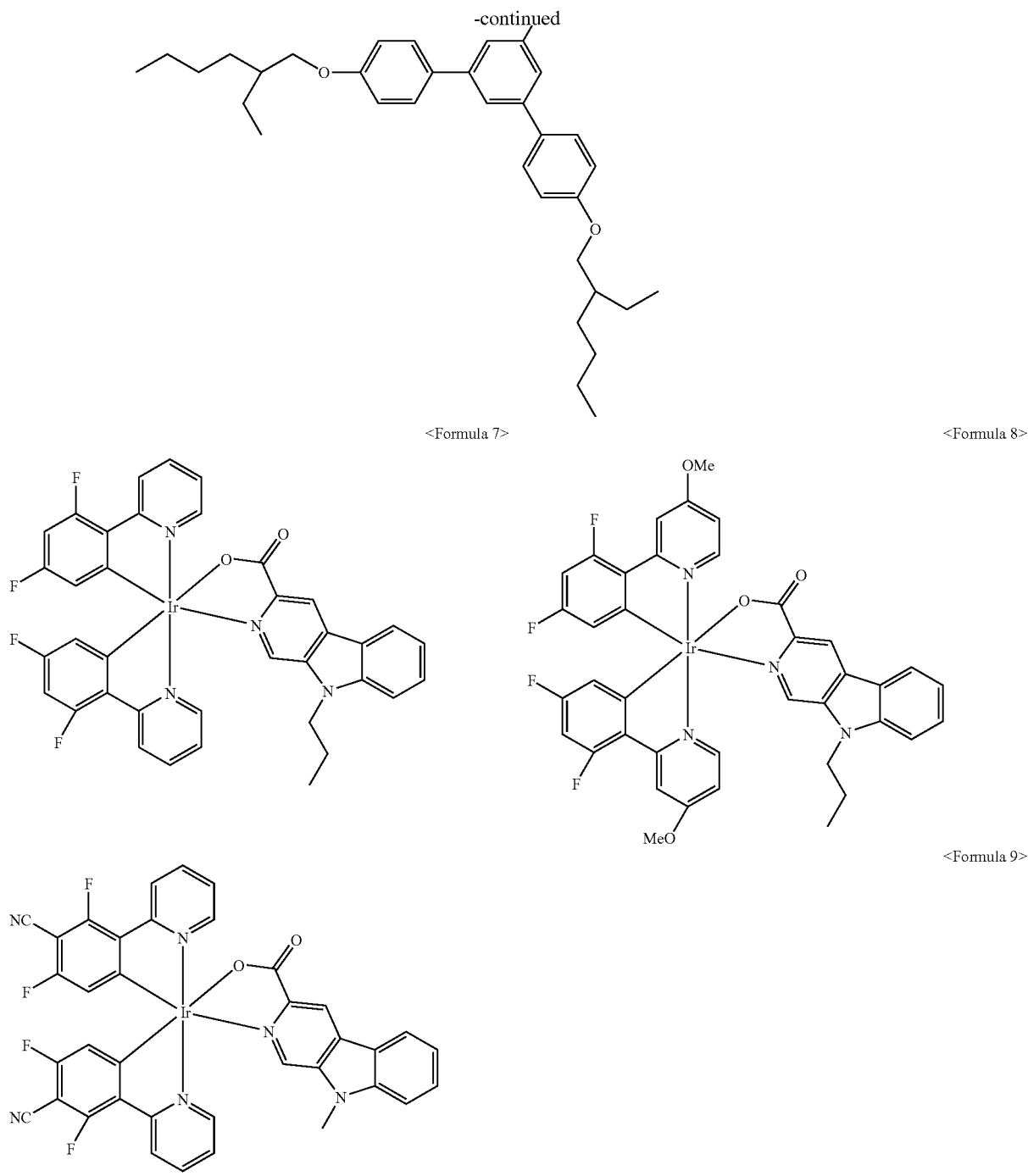

<Formula 7>

<Formula 8>

<Formula 9>

The organometallic complex of Formula 1 according to the present invention can be synthesized by the method reported by Watts group [F. O. Garces, R. J. Watts, Inorg. Chem. 1988, (27), 3464] using a [Ir(C^N)$_2$Cl]$_2$ derivative which is a starting material serving as a cyclometallating moiety donor.

An organic EL device according to the present invention is manufactured by forming an organic layer, in particular, an emitting layer, using the organometallic complex of Formula 1. Here, the organometallic complex of Formula 1 is very useful as a phosphorescent dopant which is an emitting layer material, and exhibits good emission characteristics in RGB wavelength regions. Compound of formula 1 can be used as a dopant as well as a host for materials emitting at longer wavelength than compound of formula 1. Thus it can be use for two purposes.

When the organometallic complex of Formula 1 is used as a phosphorescent dopant, the organic layer may further include at least one selected from the group consisting of at least one polymeric host, a mixture of a polymeric host and a low molecular host, a low molecular host, and a non-emission polymeric matrix. The polymeric host, the low molecular host, and the non-emission polymeric matrix are not limited provided that they are those as used commonly in formation of emitting layers for organic EL devices. Examples of the polymeric host include polyvinylcarbazole (PVK) and polyfluorene, examples of the low molecular host include CBP (4,4'-N,N'-dicarbazole-biphenyl), 4,4'-bis[9-(3,6-biphenylcarbazolyl)]-1,1'-biphenyl, 9,10-bis[(2',7'-t-butyl)-9',9"-spirobifluorenylanthracene, and tetrafluorene, and examples of the non-emission polymeric matrix include polymethylmethacrylate and polystyrene, but are not limited thereto.

The content of the organometallic complex of Formula 1 may be 1 to 30 parts by weight based on the total weight (100 parts by weight) of an organic layer forming material, e.g., an emitting layer forming material. If the content of the organometallic complex is less than 1 part by weight, device efficiency and lifetime may be lowered due to a shortage of an emitting material. On the other hand, if it exceeds 30 parts by weight, triplet quenching may occur, thereby lowering efficiency. The organometallic complex can be incorporated in an emitting layer by vacuum deposition, sputtering, printing, coating, ink-jetting, or the like.

The organometallic complex of Formula 1 can produce various color light according to a combination of a cyclometallating ligand and an auxiliary ligand. For example, the compounds of Formulae 4 and 6 above produce green light, the compound of Formula 5 above produces red light, and the compounds of Formulae 7, 8, and 9 above produce blue light. The organometallic complex can produce white light when used together with other color light-emitting material(s).

FIGS. 1A through 1F are schematic views illustrating organic EL devices according to exemplary embodiments of the present invention.

Referring to FIG. 1A, an emitting layer 12 including an organometallic complex represented by Formula 1 is disposed on a first electrode 10, and a second electrode 14 is disposed on the emitting layer 12.

Figure 1B:
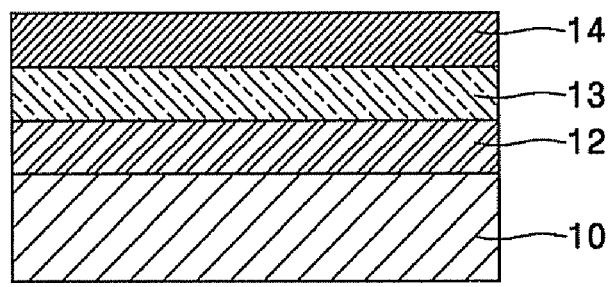

Referring to FIG. 1B, an emitting layer 12 including an organometallic complex represented by Formula 1 is disposed on a first electrode 10, a hole blocking layer (HBL) 13 is disposed on the emitting layer 12, and a second electrode 14 is disposed on the hole blocking layer 13.

Figure 1C:
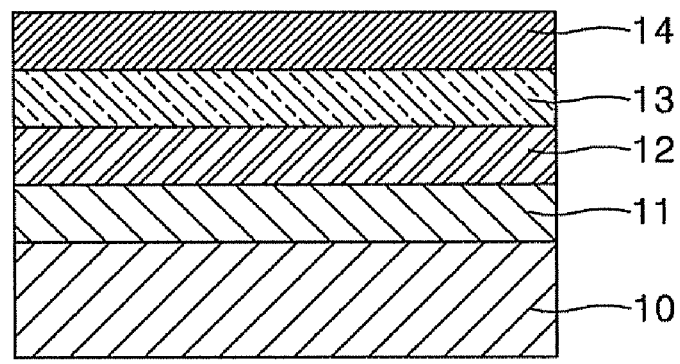

Referring to FIG. 1C, an organic EL device includes a hole injection layer (HIL) 11 between a first electrode 10 and an emitting layer 12.

Figure 1D:
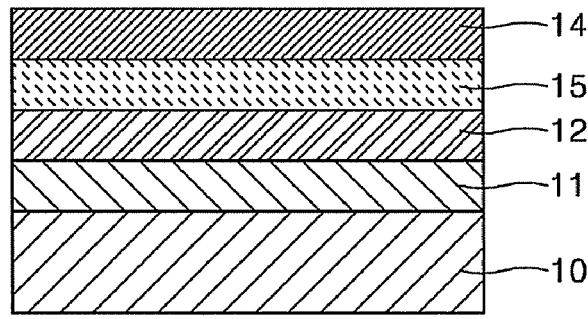

Referring to FIG. 1D, an organic EL device has the same structure as that shown in FIG. 1C except that an electron transport layer (ETL) 15 is disposed on an emitting layer 12 instead of a hole blocking layer (HBL).

Referring to 1E, an organic EL device has the same structure as that shown in FIG. 1C except that a hole blocking layer (HBL) 13 and an electron transport layer 15 are sequentially stacked on an emitting layer 12 including an organometallic complex represented by Formula 1. In some cases, an electron injection layer may be further included between the electron transport layer 15 and a second electrode 14.

Figure 1E:
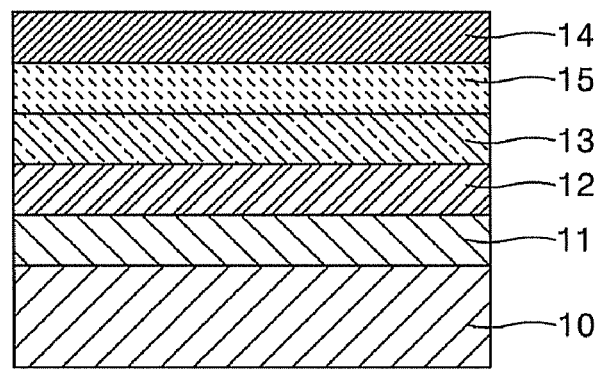
Figure 1F:
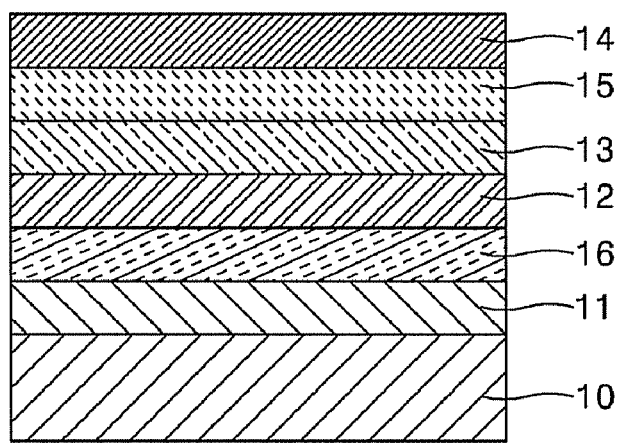

Referring to FIG. 1F, an organic EL device has the same structure as that shown in FIG. 1E except that a hole transport layer 16 is further disposed between a hole injection layer 11 and an emitting layer 12. Here, the hole transport layer 16 serves to prevent penetration of impurities derived from the hole injection layer 11 into the emitting layer 12.

The above-described organic EL devices can be manufactured by a method commonly known in the art, and the manufacture method is not particularly limited.

In the organic EL device according to the present invention, the thickness of the organic layer may be 30 to 100 nm. If the thickness of the organic layer is less than 30 nm, the efficiency and lifetime of the device may be lowered. On the other hand, if it exceeds 100 nm, a driving voltage may be increased.

As used herein, the organic layer is a layer formed of an organic compound interposed between a pair of electrodes in an organic EL device, for example an electron transport layer and a hole transport layer, in addition to an emitting layer.

In the organic EL device of the present invention, a buffer layer may be disposed between any two adjacent layers. The buffer layer may be formed of a material commonly used in the art, preferably, copper phthalocyanine, polythiophene, polyaniline, polyacetylene, polypyrrole, polyphenylenevinylene, or a derivative thereof, but is not limited thereto.

The hole transport layer may be formed of a material commonly used in the art, preferably polytriphenylamine, but is not limited thereto.

The electron transport layer may be formed of a material commonly used in the art, preferably polyoxadiazole, but is not limited thereto.

The hole blocking layer may be formed of a material commonly used in the art, preferably LiF, $BaF_2$, or $MgF_2$, but is not limited thereto.

The organic EL device according to the present invention can be manufactured by a common organic EL device manufacturing method using a common light-emitting material without requiring a particular apparatus.

The organometallic complex of Formula 1 according to the present invention can emit light in the wavelength range of about 400 to 700 nm. A light-emitting diode using such an organometallic complex can be used in optical illumination sources for full-color displays, backlighting, exterior bulletin boards, optical communication, interior decoration, and the like.

Hereinafter, the present invention will be described more specifically with reference to the following examples. The following examples are for illustrative purposes and are not intended to limit the scope of the invention.

Example 1

Synthesis of Compound Represented by Formula 4

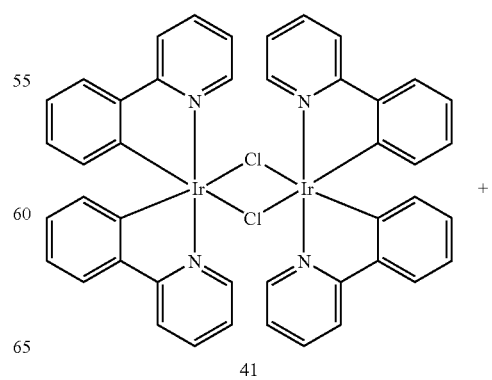

41

-continued

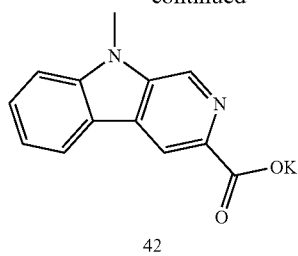

42

4

According to Reaction Scheme 1, 0.107 g of [Ir(2-phenylpyridine)$_2$Cl]$_2$ of Formula 41 and 0.25 mmol (0.628 g) of potassium beta-carbazoline-3-carboxylate of Formula 42 were dissolved in 40 ml of chloroform and 10 ml of methanol in a 250 ml side-armed flask under a nitrogen atmosphere. The reaction mixture was incubated at 50° C. for 10 hours and cooled. The reaction solution was filtered and placed under a reduced pressure to evaporate a solvent to thereby obtain a yellow powder. The yellow powder was purified on a silica column (eluent: chloroform and acetone). The resultant compound was identified as the compound of Formula 4 by $^1$H NMR and mass spectrometry. Thermogravimetric analysis showed that the decomposition temperature of the compound was 404° C. The compound showed CIE coordinates (0.23, 0.64) and an emission wavelength of 515 nm as measured in the form of a 2-methyltetrahydrofuran solution, and CIE coordinates (0.24, 0.64) and an emission wavelength of 525 nm as measured in the form of a neat film.

$^1$H-NMR (CDCl$_3$, ppm): 9.0 (s, 1H), 8.9 (d, 1H), 8.2 (d, 1H), 7.3-7.8 (m, 3H), 7.7-7.5 (m, 5H), 7.45 (d, 2H), 7.3 (t, 1H), 7.1 (t, 1H), 6.99 (t, 1H), 6.8 (dd, 3H), 6.7 (t, 1H), 6.5 (d, 1H), 6.2 (d, 1H), 3.6 (s, 3H).

Mass spectrum analysis value: [M+H$^+$] 727.1712 (calculated value: 726.16)

Example 2

Synthesis of Compound Represented by Formula 5

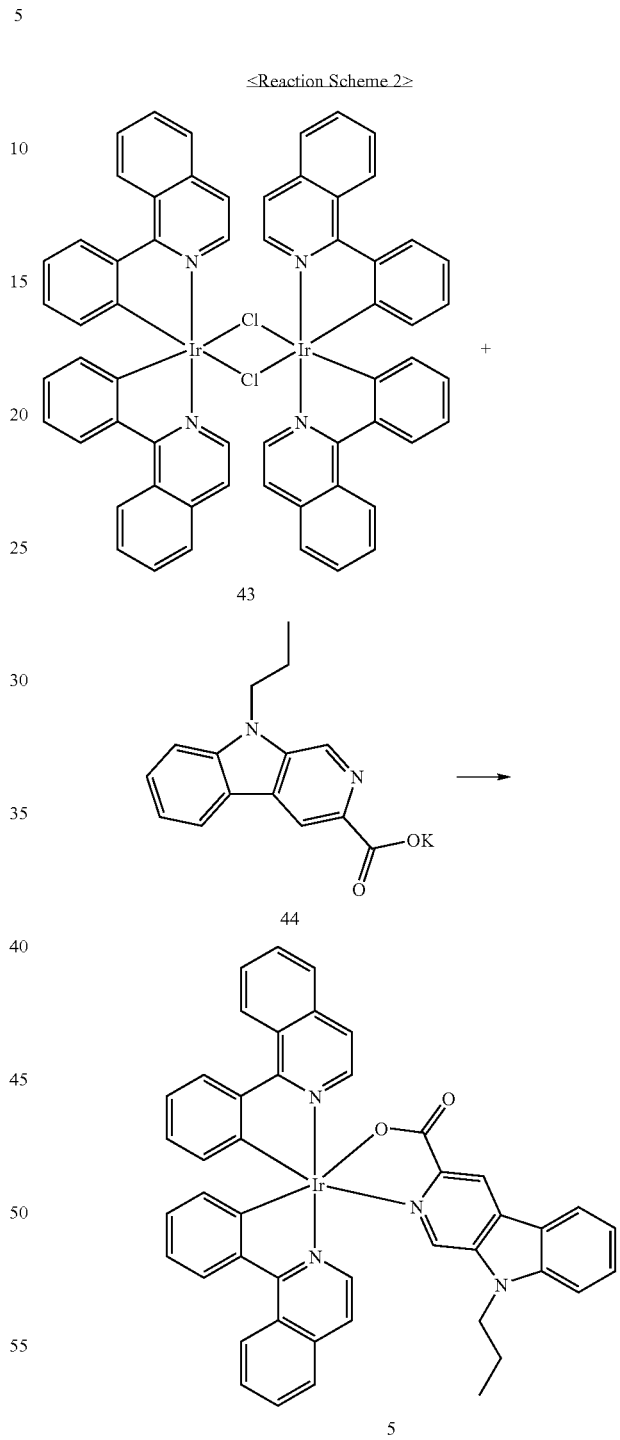

<Reaction Scheme 2>

43

44

5

According to Reaction Scheme 2, a compound of Formula 43 (0.127 g, 0.1 mmol) and a compound of Formula 44 (0.25 mmol, 0.628 g) were dissolved in 40 ml of chloroform and 10 ml of methanol in a 250 ml side-armed flask under a nitrogen atmosphere. The reaction mixture was incubated at 50° C. for 10 hours and cooled. The reaction solution was filtered and placed under a reduced pressure to evaporate a solvent to thereby obtain a yellow powder. The yellow powder was purified on a silica column (eluent: chloroform and acetone). The resultant compound was identified as the compound of Formula 5 by $^1$H NMR and mass spectrometry. Thermogravimetric analysis showed that the decomposition temperature of the compound was 330° C. The compound showed CIE coordinates (0.62, 0.36) and an emission wavelength of 605 nm as measured in the form of a 2-methyltetrahydrofuran solution, and CIE coordinates (0.62, 0.37) and an emission wavelength of 610 nm as measured in the form of a neat film.

$^1$H-NMR (CDCl$_3$, ppm): 9.03 (s, 1H), 9.02-8.9 (m, 2H), 8.8 (d, 1H), 8.31-8.18 (m, 3H), 7.9 (t, 1H), 7.8 (t, 1H), 7.77-7.67 (m, 4H), 7.62 (t, 1H), 7.56 (s, 1H), 7.49 (d, 1H), 7.45-7.31 (m, 3H), 7.18 (d, 1H), 7.01 (t, 1H), 6.95 (t, 1H), 6.90 (t, 1H), 6.75 (t, 1H), 6.64 (d, 1H), 6.30 (d, 1H), 3.96 (m, 2H), 1.63 (t, 2H), 0.75 (t, 3H).

Mass spectrum analysis value: [M+H$^+$] 855.2 (calculated value: 854.2)

Example 3

Synthesis of Compound Represented by Formula 6

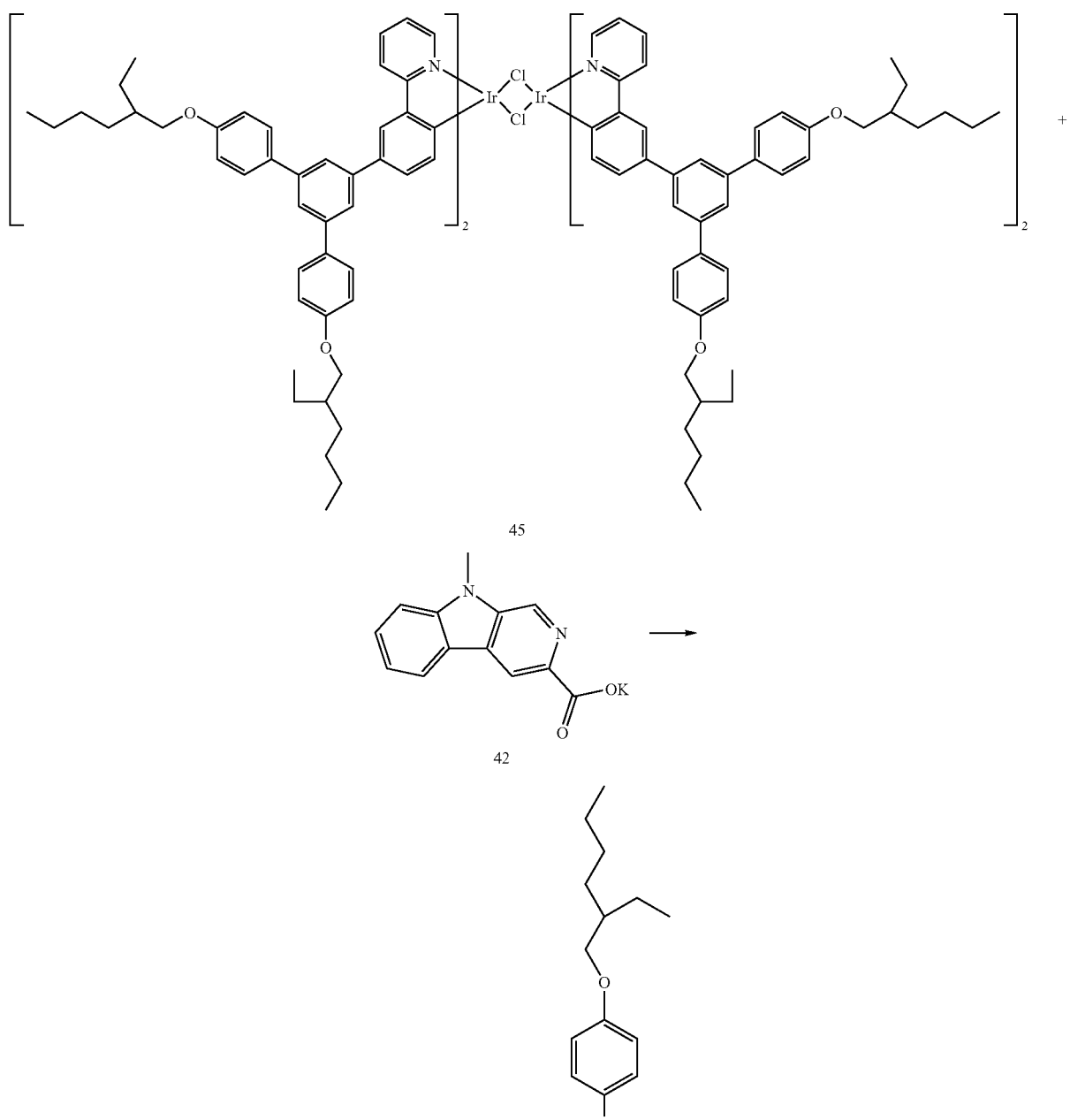

-continued

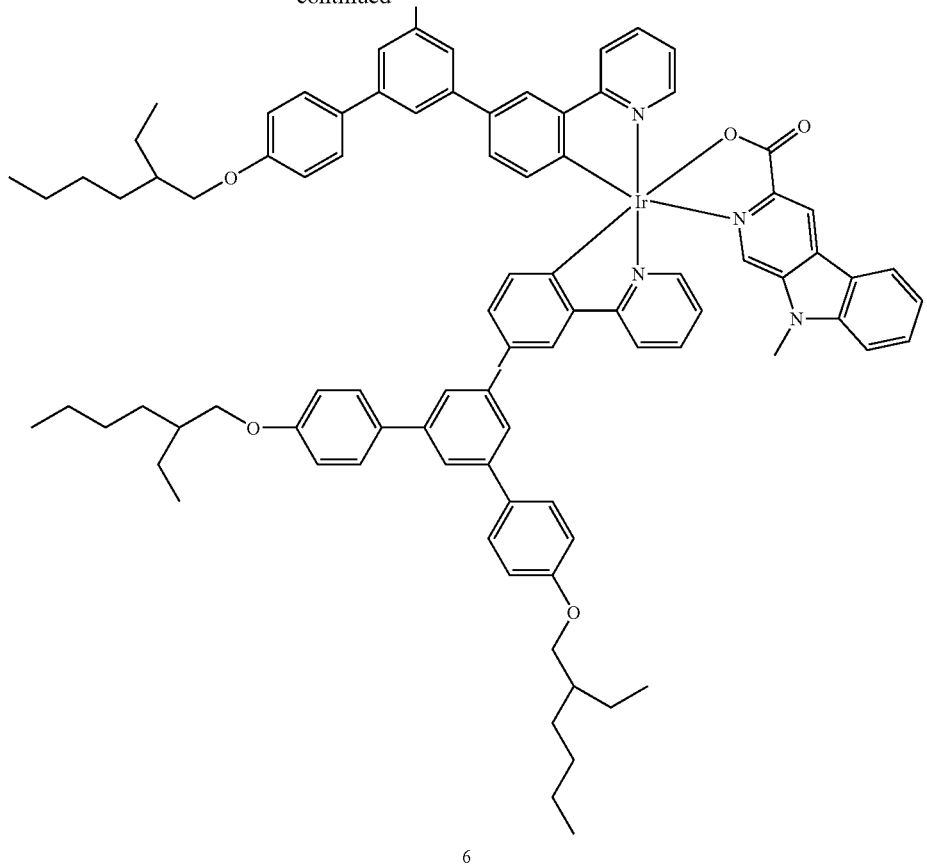

6

According to Reaction Scheme 3, a compound of Formula 45 (0.301 g, 0.1 mmol) and potassium beta-carbazolin-3-carboxylate of Formula 42 (0.25 mmol, 0.628 g) were dissolved in 40 ml of chloroform and 10 ml of methanol in a 250 ml side-armed flask under a nitrogen atmosphere. The reaction mixture was incubated at 50° C. for 10 hours and cooled. The reaction solution was filtered and placed under a reduced pressure to evaporate a solvent to thereby obtain a yellow powder. The yellow powder was purified on a silica column (eluent: chloroform and acetone). The resultant product was further purified by reprecipitation from chloroform and a methanol solution. The resultant compound was identified as the compound of Formula 6 by $^1$H NMR and mass spectrometry. The compound showed CIE coordinates (0.28, 0.65) and an emission wavelength of 527 nm as measured in the form of a 2-methyltetrahydrofuran solution, and CIE coordinates (0.29, 0.65) and an emission wavelength of 531 nm as measured in the form of a neat film.

$^1$H-NMR (CDCl$_3$, ppm): 9.07 (s, 1H), 8.99 (d, 1H), 8.22 (d, 1H), 8.09-7.90 (m, 5H), 7.75 (t, 4H), 7.70-7.56 (m, 13H), 7.51 (d, 1H), 7.49-7.35 (m, 2H), 7.32 (d, 1H), 7.18 (t, 2H), 7.02 (t, 8H), 6.91 (t, 1H), 6.70 (d, 1H), 6.44 (d, 1H), 3.92 (dd, 8H), 3.74 (s, 3H), 1.78 (m, 4H), 1.57-1.40 (m, 16H), 1.40-1.29 (m, 16H), 1.03-0.88 (m, 24H).

Mass spectrum analysis value: [M+H$^+$] 1696.3 (calculated value: 1695.2)

Example 4

Synthesis of Compound Represented by Formula 7

<Reaction Scheme 4>

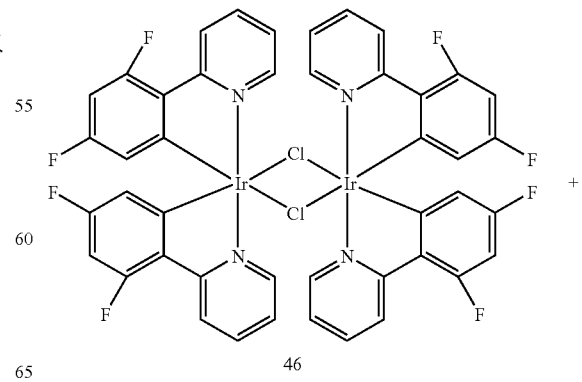

46

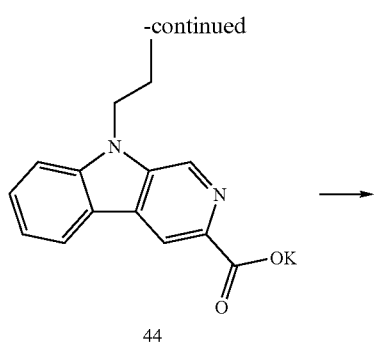

44

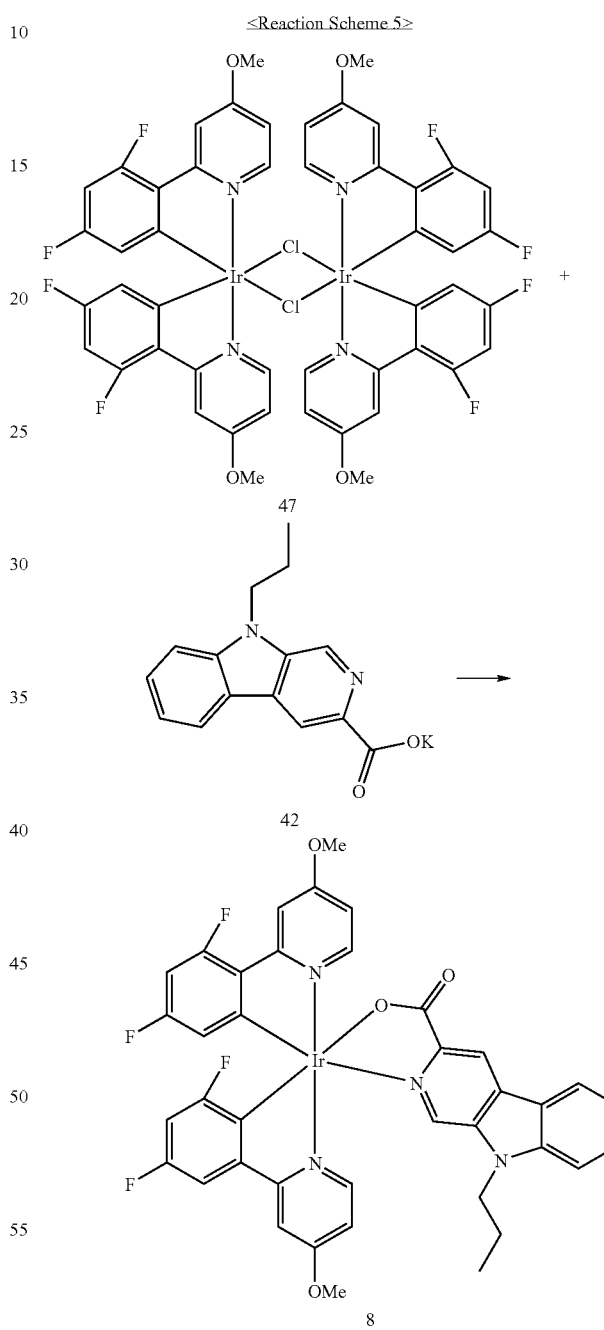

7

According to Reaction Scheme 4, a compound of Formula 46 (0.121 g, 0.1 mmol) and a compound of Formula 44 (0.25 mmol, 0.660 g) were dissolved in 40 ml of chloroform and 10 ml of methanol in a 250 ml side-armed flask under a nitrogen atmosphere. The reaction mixture was incubated at 50° C. for 10 hours and cooled. The reaction solution was filtered and placed under a reduced pressure to evaporate a solvent to thereby obtain a yellow powder. The yellow powder was purified on a silica column (eluent: chloroform and acetone). The resultant compound was identified as the compound of Formula 7 by $^1$H NMR and mass spectrometry. Thermogravimetric analysis showed that the decomposition temperature of the compound was 330° C. The compound showed CIE coordinates (0.13, 0.31) and an emission wavelength of 471 nm as measured in the form of a 2-methyltetrahydrofuran solution, and CIE coordinates (0.13, 0.35) and an emission wavelength of 476 nm as measured in the form of a neat film.

Example 5

Synthesis of Compound Represented by Formula 8

<Reaction Scheme 5>

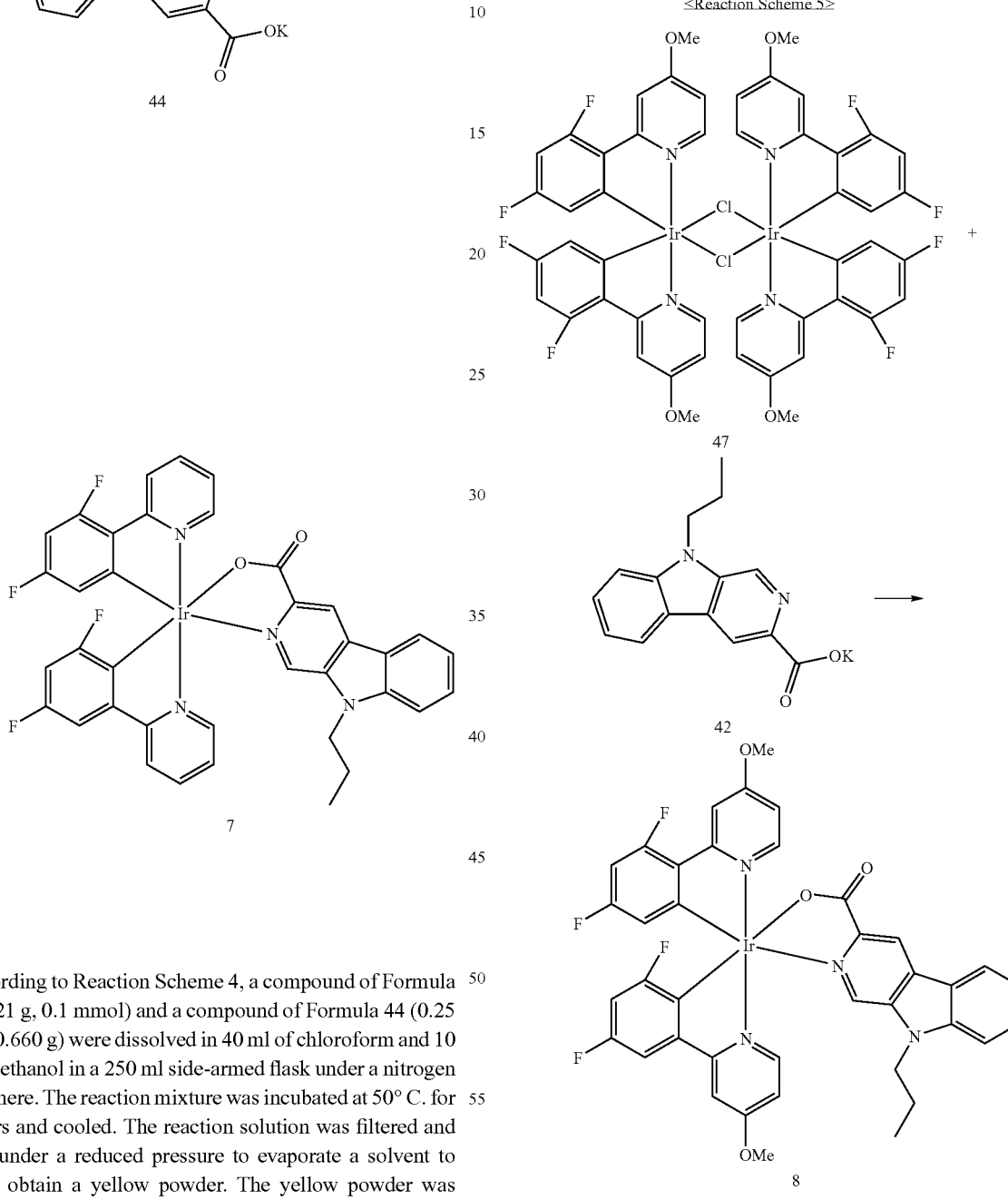

According to Reaction Scheme 5, a compound of Formula 47 (0.133 g, 0.1 mmol) and a compound of Formula 42 (0.25 mmol, 0.660 g) were dissolved in 40 ml of chloroform and 10 ml of methanol in a 250 ml side-armed flask under a nitrogen atmosphere. The reaction mixture was incubated at 50° C. for 10 hours and cooled. The reaction solution was filtered and placed under a reduced pressure to evaporate a solvent to thereby obtain a yellow powder. The yellow powder was purified on a silica column (eluent: chloroform and acetone). The resultant compound was identified as the compound of Formula 8 by $^1$H NMR and mass spectrometry. Thermogravimetric analysis showed that the decomposition temperature of the compound was 330° C. The compound showed CIE coordinates (0.13, 0.25) and an emission wavelength of 465 nm as measured in the form of a 2-methyltetrahydrofuran solution, and CIE coordinates (0.14, 0.27) and an emission wavelength of 469 nm as measured in the form of a neat film.

Example 6

Synthesis of Compound Represented by Formula 9

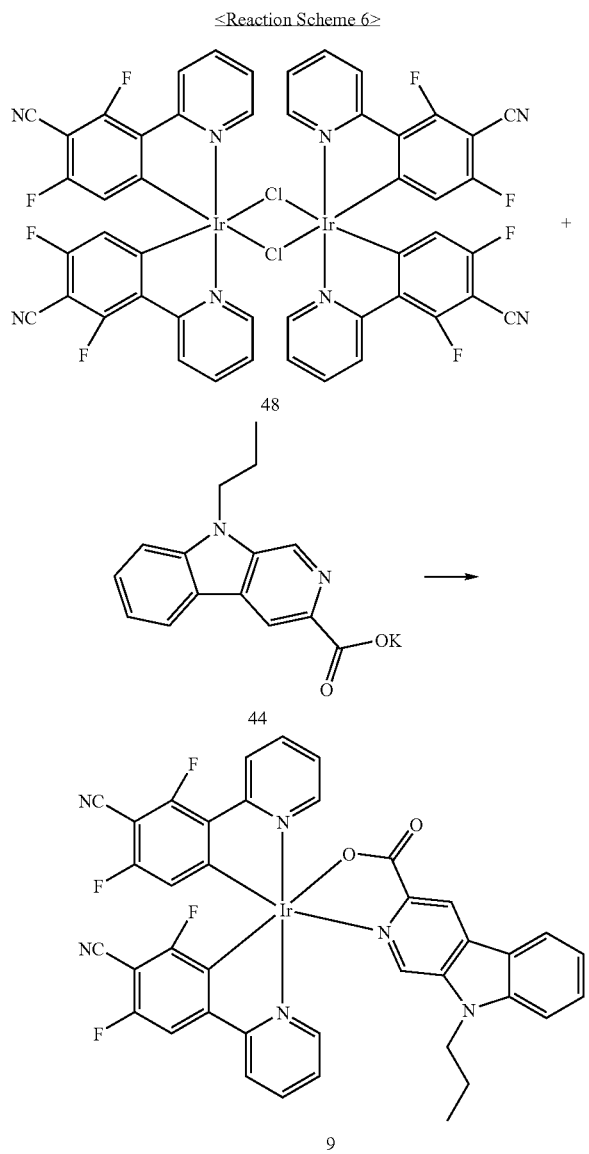

According to Reaction Scheme 6, a compound of Formula 48 (0.132 g, 0.1 mmol) and a compound of Formula 44 (0.25 mmol, 0.660 g) were dissolved in 40 ml of chloroform and 10 ml of methanol in a 250 ml side-armed flask under a nitrogen atmosphere. The reaction mixture was incubated at 50° C. for 10 hours and cooled. The reaction solution was filtered and placed under a reduced pressure to evaporate a solvent to thereby obtain a yellow powder. The yellow powder was purified on a silica column (eluent: chloroform and acetone). The resultant compound was identified as the compound of Formula 9 by $^1$H NMR and mass spectrometry. Thermogravimetric analysis showed that the decomposition temperature of the compound was 330° C. The compound showed CIE coordinates (0.15, 0.23) and an emission wavelength of 465 nm as measured in the form of a 2-methyltetrahydrofuran solution, and CIE coordinates (0.16, 0.24) and an emission wavelength of 468 nm as measured in the form of a neat film.

The compounds obtained in Examples 1-6 can be used to form dopants with good phosphorescent characteristics. In particular, due to a strong electronic effect caused by substituent introduction, the compounds are suitable as phosphorescent materials emitting light in various emission wavelength ranges.

In particular, the compound obtained in Example 1 exhibited a decomposition temperature of 404° C. as measured by thermogravimetric analysis, indicating very good thermal stability. This shows that the compound has good resistance against sintering, etc. during device fabrication.

Manufacture of Organic EL Devices

Example 7

ITO (indium tin oxide)-coated transparent electrode substrates were cleaned and ITO was then patterned using a photoresist resin and an etchant to form ITO electrode patterns. The ITO electrode patterns were again cleaned. PEDOT{poly(3,4-ethylenedioxythiophene)}[CH8000] was coated to a thickness of about 140 nm on the ITO electrode patterns, and baked at 80° C. for about five minutes to form hole injection layers.

A solution of TPBI, TPD (TPBI:TPD=1:1), and 5 wt % of the compound of Formula 4 as a dopant in dichloromethane was spin-coated on the hole injection layers to form emitting layers with a thickness of 35 nm. Then, TPBI was vacuum-deposited on the emitting layers using a vacuum depositor under a vacuum level of 4×10$^{-6}$ torr or less to form electron transport layers with a thickness of 40 nm and LiF was vacuum-deposited on the electron transport layers to form electron injection layers with a thickness of 1 nm.

Figure 2:
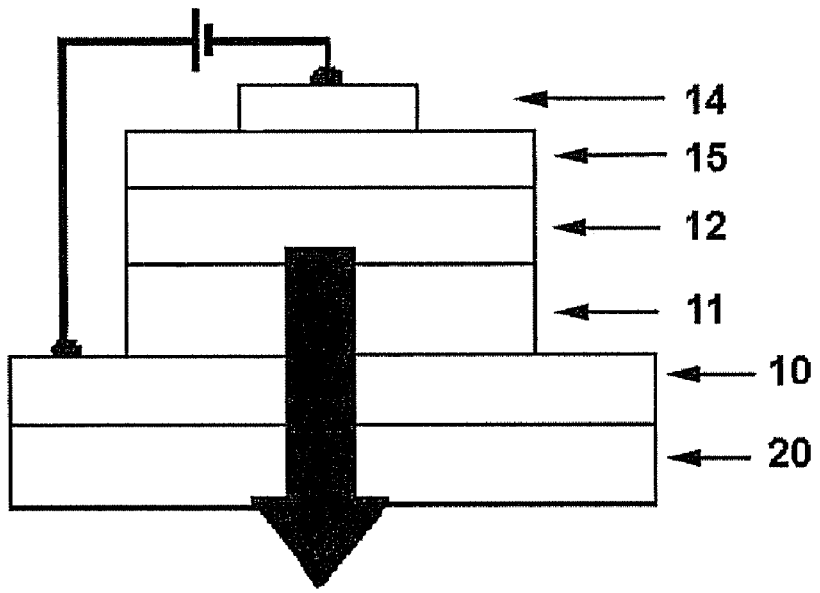
FIG. 2 is a view illustrating an organic EL device manufactured according to an embodiment of the present invention.

Next, Al was deposited at a rate of 10 Å/sec to form anodes with a thickness of 150 nm. The resultant structures were encapsulated to complete organic EL devices. Here, the encapsulation was performed by adhering glass substrates attached with a moisture absorber using a UV curing agent in a Glove box prepared to have a dry nitrogen atmosphere. The organic EL devices had a structure of ITO/PEDOT-PSS (140 nm)/TPBI-TPD (1:1)-dopant 5 wt % (35 nm)/TPBI (40 nm)/ LiF (0.8 nm)/Al(150 nm). The organic EL devices were multi-layered devices and are schematically illustrated in FIG. 2. The emission areas of the organic EL devices were 6 mm$^2$.

The maximum emission efficiencies $\eta_L$, $\eta_P$, and $\eta_{ex}$ of the organic EL devices were respectively 14.5 cd/A, 9.15 lm/w, and 5% at 0.002 mA and 5V.

Example 8

Organic EL devices were manufactured in the same manner as in Example 7 except that the compound of Formula 6 (synthesized in Example 3) was used instead of the compound of Formula 4 (synthesized in Example 1).

The maximum emission efficiencies $\eta_L$, $\eta_P$, and $\eta_{ex}$ of the organic EL devices were respectively 32.8 cd/A, 29.4 lm/w, and 10.7% at 0.002 mA and 5V.

These results show that compounds according to the present invention can be efficiently used in green light-emitting phosphorescent organic EL devices.

TABLE 1

| Section | EL $\lambda_{max}$ (nm) | CIE (x, y) at 10 mA | Maximum efficiency $\eta_L$(cd/A) | Maximum efficiency $\eta_P$ (lm/W) | Maximum efficiency $\eta_{ex}$ (%) | Current density (mA/cm$^2$) | Driving voltage (V) |
|---|---|---|---|---|---|---|---|
| Example 7 | 510 | 0.28, 0.58 | 15.2 | 11.9 | 5.8 | 0.03 | 3 |
| Example 8 | 525 | 0.34, 0.60 | 32.8 | 29.4 | 10.7 | 0.06 | 3 |

As can be seen from Table 1, an organic EL device employing a compound according to the present invention exhibits high brightness and current density, and can be operated even at low voltages.

Example 9

We have investigated soluble processed red emitting OLEDs utilizing the phosphorescent host-dopant system.

Both the host and dopant materials are the bis-cyclometalated Ir(III) complexes. The dopant [(piq)$_2$Irobt] of the formula 51 is a heteroleptic red emitting Ir(III) complex with phenyl quinoline as the cyclometalating (C^N) ligand and a triazole derivative (2-hydroxy-5-methyl-phenyl benzotriazole, obt) as the ancillary ligand. The complex emits from the admixture of ligand-centered and $^3$MLCT states at 616 nm with a photoluminescence quantum efficiency of 41% relative to Irpiq$_3$ (45%). The host is the dendrimeric complex [(Dppy)$_2$Ir mcac] of the formula 6.

<Formula 6>

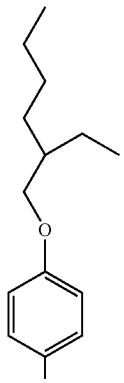
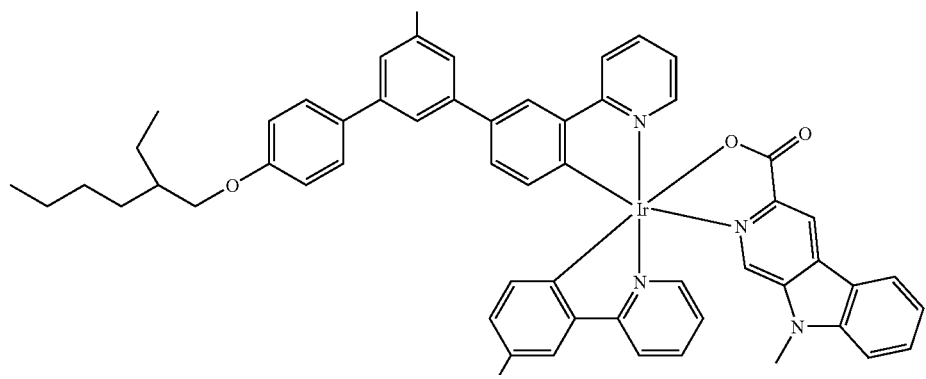

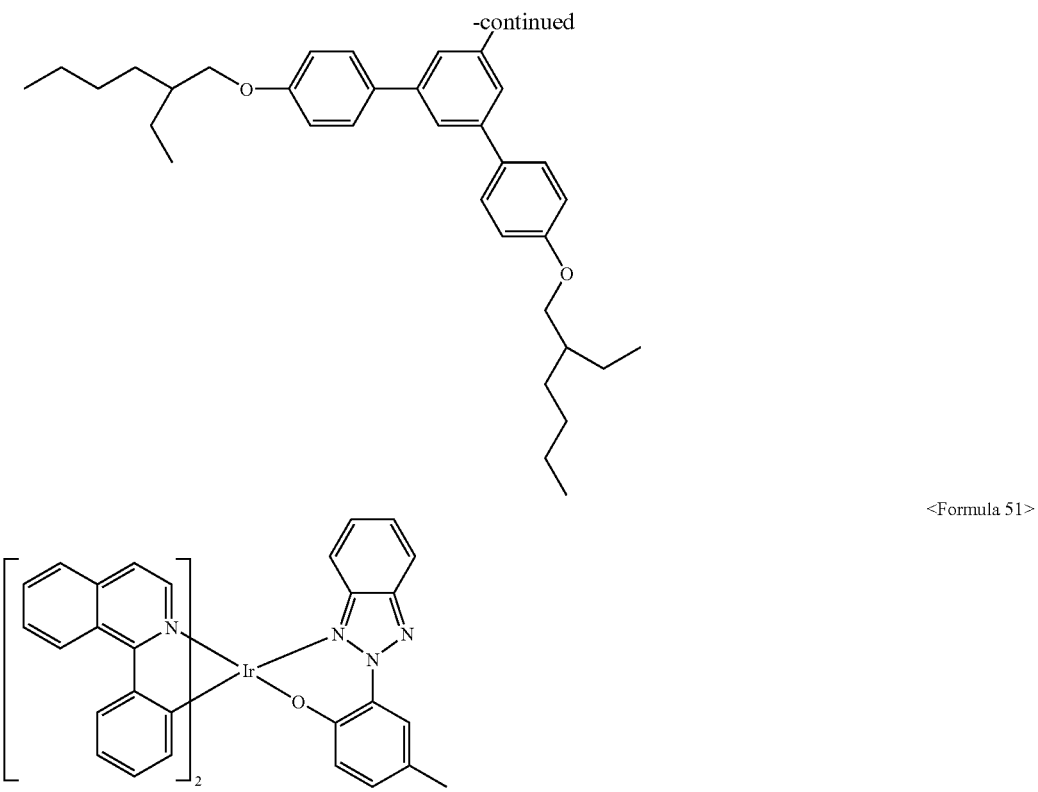

<Formula 51>

The devices are fabricated by dissolving 40 mg of the host and dopant (1, 2, 4, 6, 8 and 12% doping ratio) in 0.96 mL of chloroform and then spin coating on a precoated PEDOT-PSS film (40 nm) on ITO to obtain an emitting layer of thickness of 75 nm. The hole blocking and electron transporting layer of TPBI of thickness 45 nm was deposited on the emitting layer by the thermal evaporation process. This was followed by the subsequent deposition of LiF (1 nm) and Al (150 nm) to form the cathode.

Figure 3:
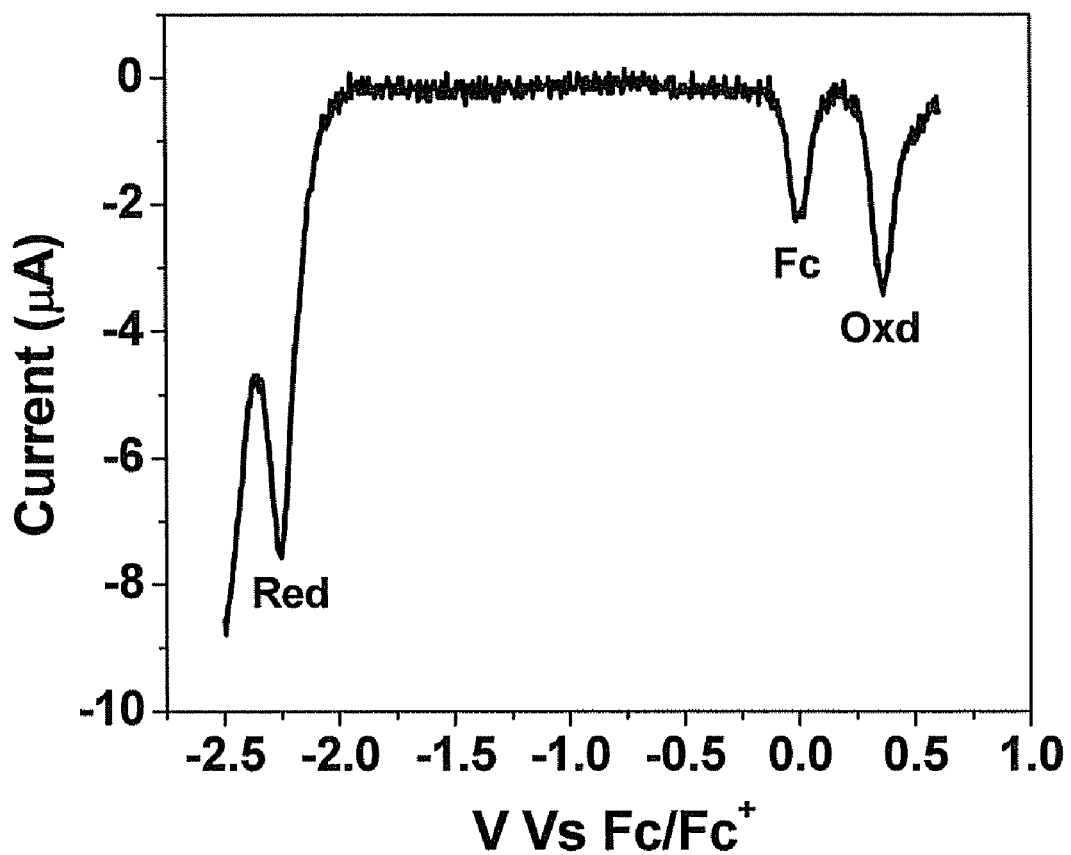
FIGS. 3 and 4 show Oxidation and reduction potentials of the dopant of Example 9 by square wave voltammetry
Figure 4:
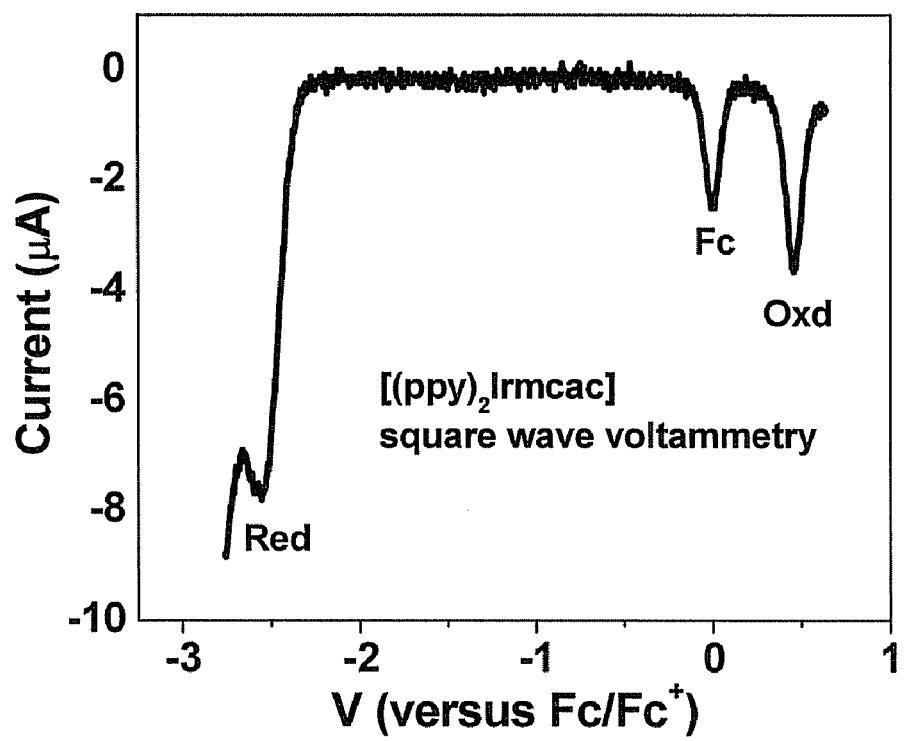

The HOMO and LUMO levels are determined from the square wave voltametric method using ferrocene/Ferrocenium as the internal standard. The Oxidation and reduction potentials of the dopant [(piq)$_2$ Ir obt] and the host [(dppy)$_2$ Ir mcac] are given in the plots in the FIGS. 3 and 4.

Figure 5:
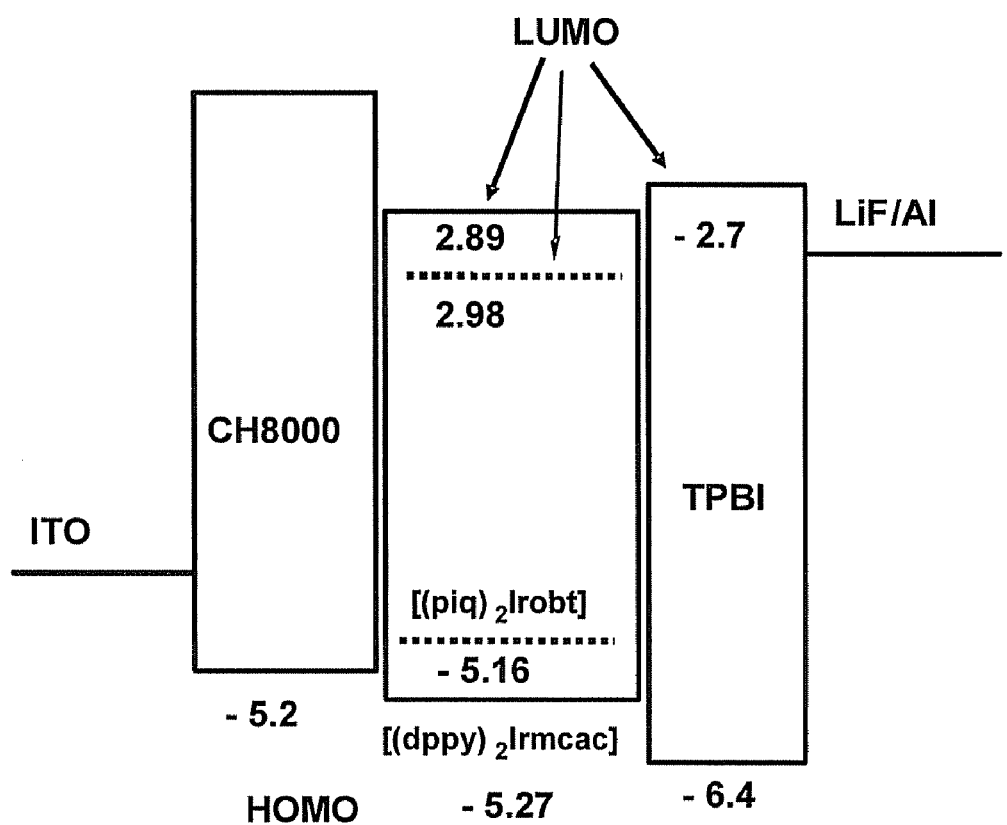
FIG. 5 shows the energy levels of the materials used in the device fabrication of Example 9.
Figure 6:
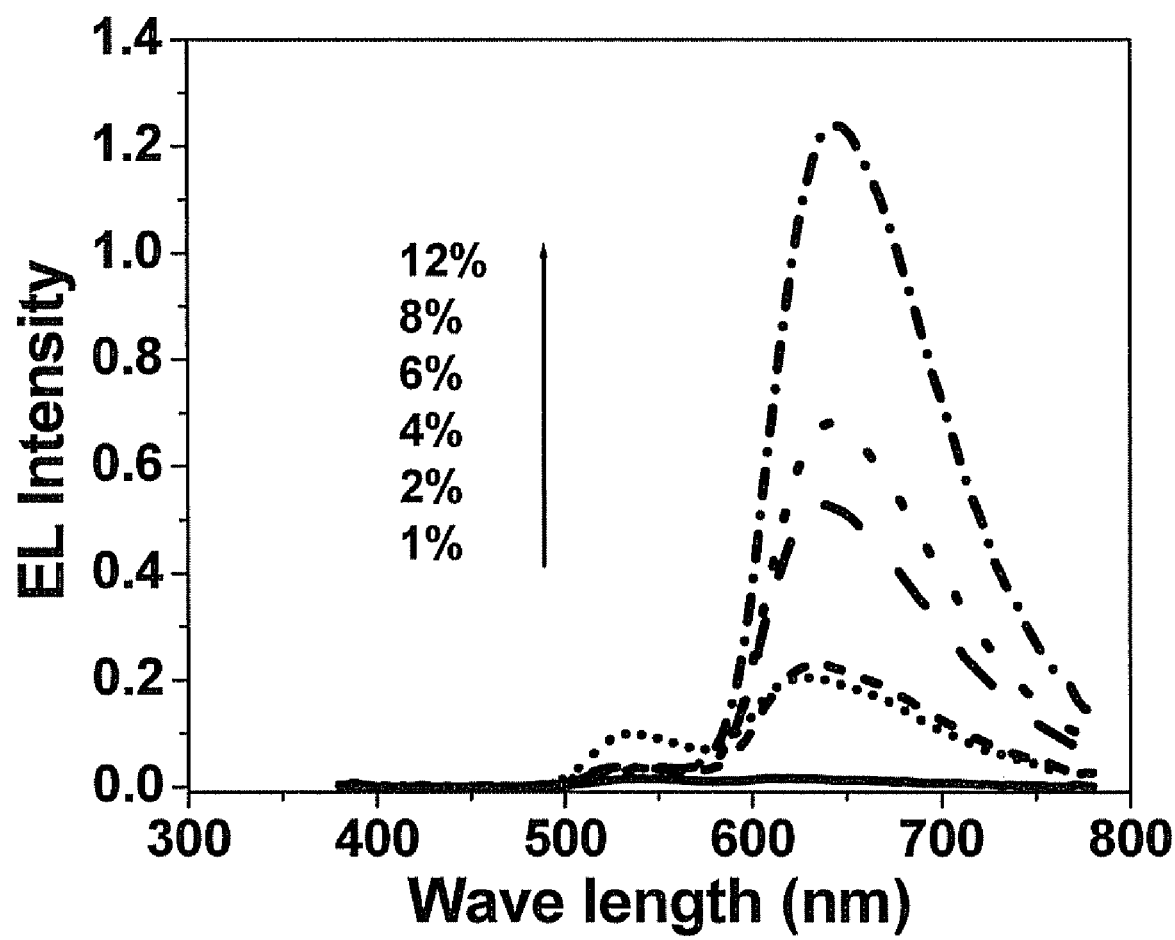
FIG. 6 shows the EL spectra at different doping concentrations of the device according to the Example 9.
Figure 7:
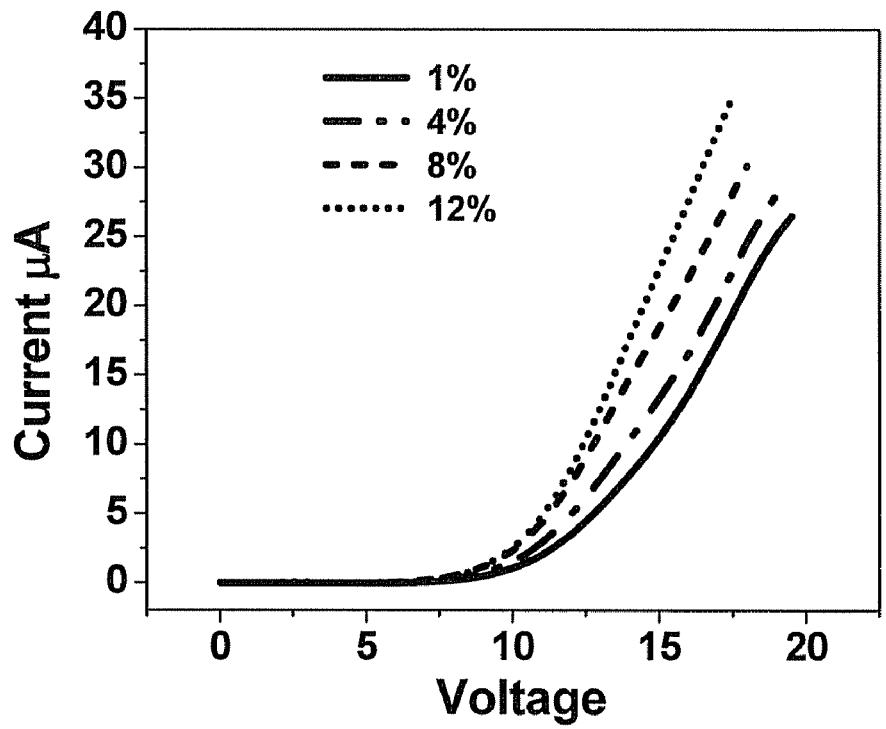
FIG. 7 shows the current-voltage characteristics of the device according to the Example 9.
Figure 8:
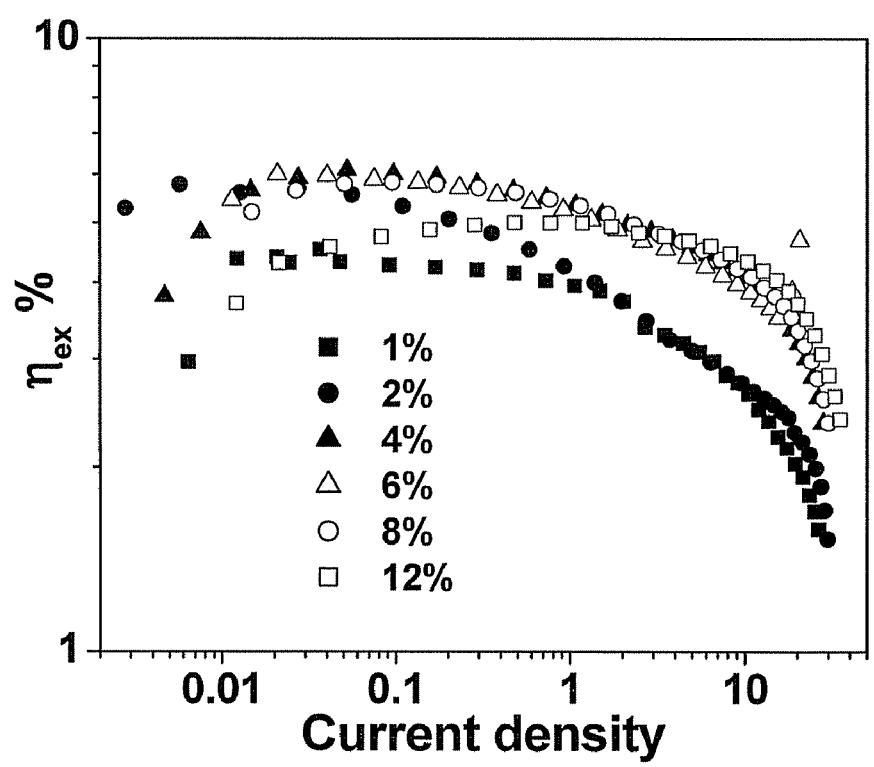
FIG. 8 shows the $\eta_{ex}$ versus current density of the device according to the Example 9.

The energy levels of the materials used in the device fabrication are given in the FIG. 5. The EL spectra at different doping concentrations in FIG. 6 shows that the energy is completely transferred from the green phosphorescent host to the red phosphorescent dopant at 12% doping concentration. The FIGS. 7 and 8 show the current-voltage characteristics and $\eta_{ex}$ versus current density of the devices. Higher current densities of the devices with increasing doping concentrations can be attributed to two effects; 1) the increase in the doping concentration favors more electron injection into the dopant from TPBI as well as the host with the subsequent recombination with the holes injected from both the PEDOT layer and the host into the dopant and 2) with the increase in the doping concentration the alkyl chains in the host skeleton hindering the charge hopping are reduced there by increasing the charge hopping on the aromatic ligands of the phosphorescent host and guest. The external quantum efficiency ($\eta_{ex}$) increases with the increase in the doping concentration from 4.36% for 1% to 6.1% for 4% doping concentrations, respectively. The value remains around 6% until the 8% doping concentration which further decreases to 5% for 12% doping concentration. This can be attributed to the quenching of the excitons on the dopant at higher doping concentration.

Figure 9:
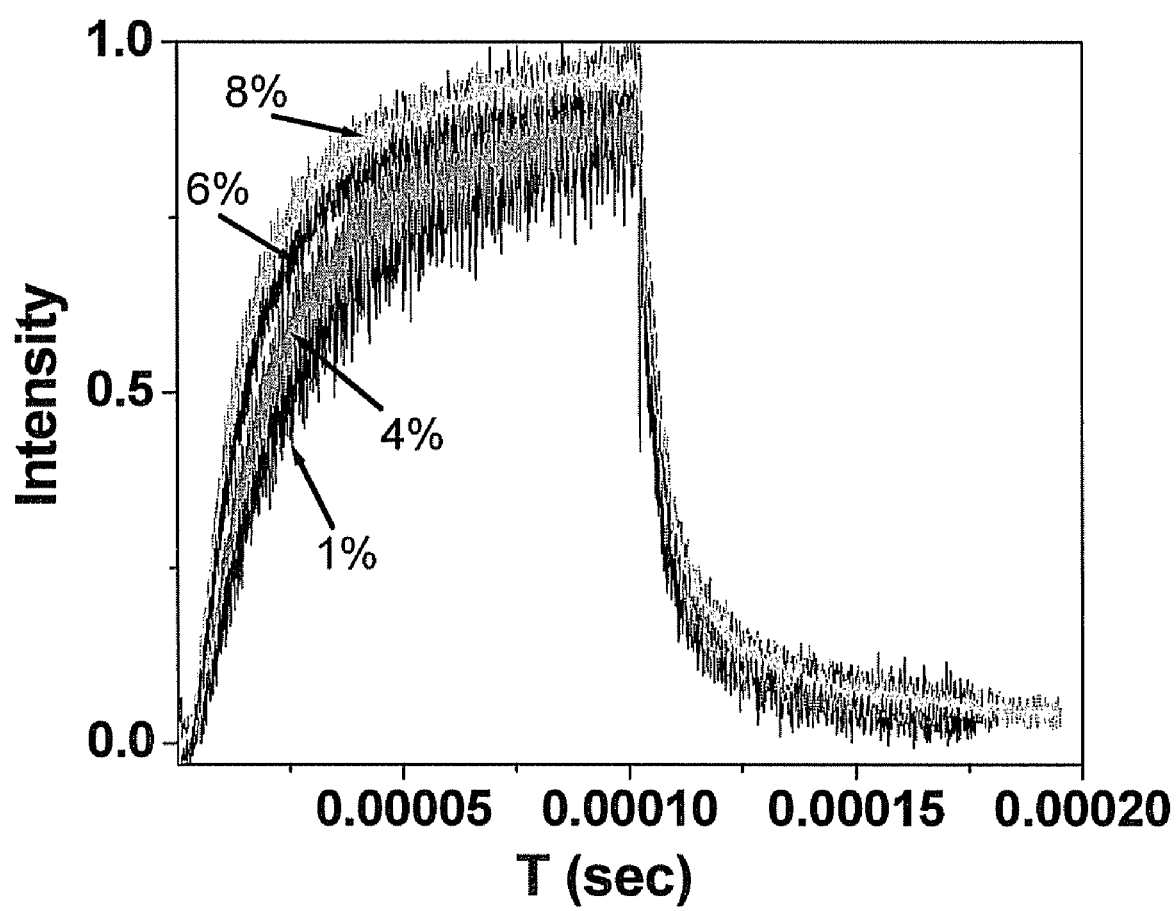
FIG. 9 shows the transient EL measurements of the 4, 6, and 8% doped devices according to the Example 9.

The transient EL measurements of the 4, 6 and 8% doped devices are shown in the FIG. 9. It demonstrates that with the increase in the doping concentration the rate of exciton formation is increased and the rising time (tr) is decreased. For the 4, 6 and 8% doped devices the tr is found to be 29.2, 21.6 and 19.8 μs respectively, indicating that the higher doping concentration helps in the quicker rate of exciton formation by charge transporting which is supported by a favorable energy level alignment. The EL decay time is also shown to increase with the increase in the doping concentration. We presume, the increased doping concentration helps in an efficient triplet transfer from the host as found in the suppressed green emission at higher doping concentrations. Another feature observed in the transient EL spectra is that the rate of exciton formation and tr as regards to the 540 nm green emission is not affected by the doping concentrations at 4, 6 and 8%.

The EL performances are given in the table 2.

TABLE 2

|  | 1% | 2% | 4% | 6% | 8% | 12% |
|---|---|---|---|---|---|---|
| $\eta_{ex}$ % | 4.32 | 5.68 | 6.1 | 6 | 5.81 | 5.01 |
| $\eta_{ex}$ % (100 cd/m2) | 3.88 | 3.72 | 4.93 | 4.54 | 4.66 | 4.67 |
| $\eta_L$ Cd/A | 7.4 | 6.54 | 4.53 | 3.44 | 2.92 | 2.13 |
| $\eta_P$ Lm/W | 3.88 | 4.49 | 2.29 | 1.92 | 1.58 | 0.98 |
| Turn on V | 6 | 4 | 4.5 | 5 | 5 | 5 |
| (x, y) | 0.46, 0.51 | 0.51, 0.46 | 0.60, 0.39 | 0.63, 0.36 | 0.64, 0.34 | 0.67, 0.32 |

An organometallic complex according to the present invention can efficiently emit light. Such an organometallic complex can be used in formation of an organic layer of an organic EL device, and can emit light in the wavelength range of 400-700 nm as a highly efficient phosphorescent material.
wherein,
$R_{11}$, $R_{12}$, $R_{13}$, $R_{14}$, and $R_{15}$ are each independently a monosubstituted or polysubstituted functional group selected from hydrogen, a halogen atom, —OR, —N(R)$_2$, —P(R)$_2$, —POR, —PO$_2$R, —PO$_3$R, —SR, —Si(R)$_3$, —B(R)$_2$, —B(OR)$_2$, —C(O)R, —C(O)OR, —C(O)N(R), —CN, —NO$_2$, —SO$_2$, —SOR, —SO$_2$R, —SO$_3$R, a C$_1$-C$_{20}$ alkyl group, and a C$_6$-C$_{20}$ aryl group where R is selected from hydrogen, a halogen atom, a substituted or unsubstituted C$_1$-C$_{20}$ alkyl group, a substituted or

What is claimed is:

1. An organometallic complex represented by Formula 2 below:

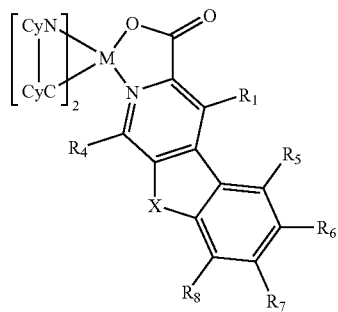

<Formula 2> wherein,
M is Ir, Os, Pt, Pb, Re, Ru, or Pd;
CyN is a substituted or unsubstituted C3-C60 heterocyclic group comprising nitrogen bound to M or a substituted or unsubstituted C3-C60 heteroaryl group comprising nitrogen bound to M;
CyC is a substituted or unsubstituted C4-C60 carbocyclic group comprising carbon bound to M, a substituted or unsubstituted C3-C60 heterocyclic group comprising carbon bound to M, a substituted or unsubstituted C6-C60 aryl group comprising carbon bound to M, or a substituted or unsubstituted C3-C60 heteroaryl group comprising carbon bound to M;
CyN-CyC is a cyclometalating ligand bound to M via nitrogen (N) and carbon (C);
X is NR$_a$, O, S, SiR$_b$R$_c$ or CR$_d$R$_e$;
$R_1$, $R_4$, $R_5$, $R_6$, $R_7$, $R_8$, $R_a$, $R_b$, $R_c$, $R_d$, and $R_e$ are each independently hydrogen, a hydroxyl group, a sulfo group, a halogen atom, a carboxyl group, an amino group, a nitro group, a cyano group, a substituted or unsubstituted C$_1$-C$_{20}$ alkyl group, a substituted or unsubstituted C$_1$-C$_{20}$ alkoxy group, a substituted or unsubstituted C$_2$-C$_{20}$ alkenyl group, a substituted or unsubstituted C$_2$-C$_{20}$ alkynyl group, a substituted or unsubstituted C$_1$-C$_{20}$ heteroalkyl group, a substituted or unsubstituted C$_6$-C$_{30}$ aryl group, a substituted or unsubstituted C$_6$-C$_{30}$ aryloxy group, a substituted or unsubstituted C$_2$-C$_{20}$ alkoxycarbonyl group, a substituted or unsubstituted C$_1$-C$_{20}$ acyloxy group, a substituted or unsubstituted C$_1$-C$_{20}$ acylamino group, a substituted or unsubstituted C2-C20 alkoxycarbonylamino group, a substituted or unsubstituted C$_7$-C$_{30}$ aryloxycarbonylamino group, a sulfonylamino group, a sulfamoyl group, a carbamoyl group, a substituted or unsubstituted C$_6$-C$_{30}$ arylthio group, a substituted or unsubstituted C3-C30 heteroarylthio group, a sulfonyl group, a sulfinyl group, an ureido group, a phosphoric acid amido group, a hydroxaminic group, a sulfino group, a hydrazine group, an imino group, a silyl group, a phosphino group, a phosphinyl a substituted or unsubstituted C4-C30 cycloalkyl group, a substituted or unsubstituted C$_7$-C$_{30}$ arylalkyl group, a substituted or unsubstituted C$_5$-C$_{30}$ heteroaryl group, or a substituted or unsubstituted C$_3$-C$_{30}$ heteroarylalkyl group.

2. The organometallic complex of claim 1, wherein the compound of Formula 2 is selected from compounds represented by Formulae 4 through 9 below:

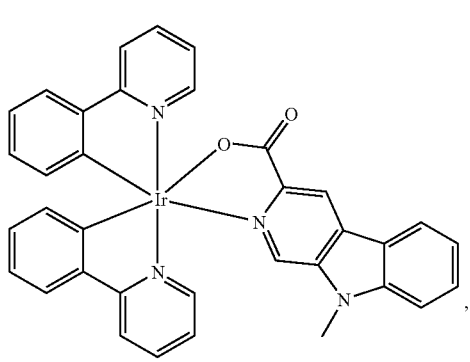

<Formula 4>

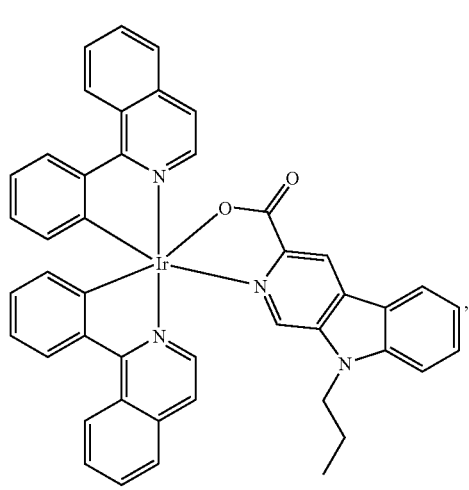

<Formula 5>

<Formula 6>
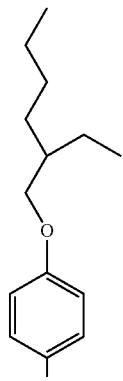
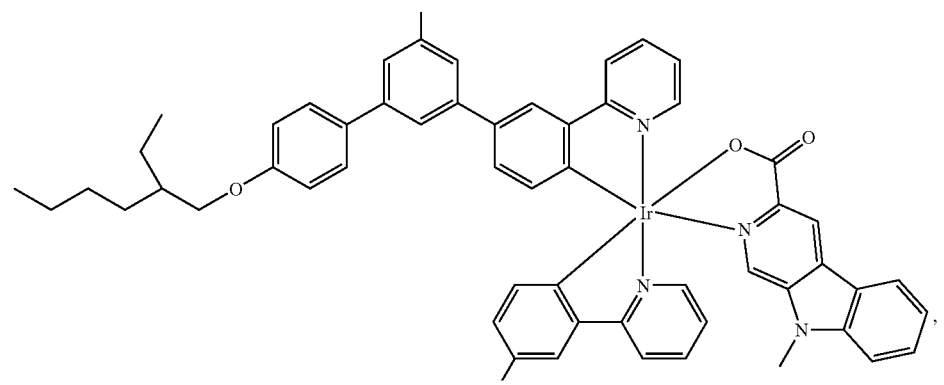
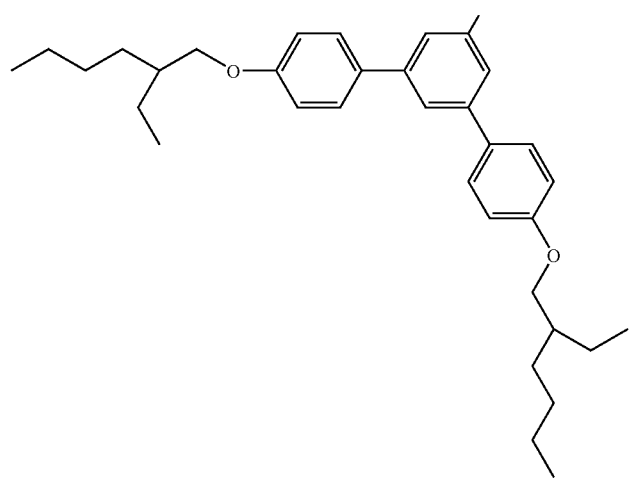

<Formula 7>
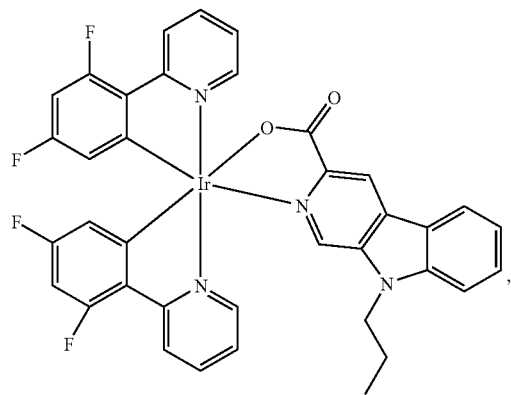
<Formula 8>
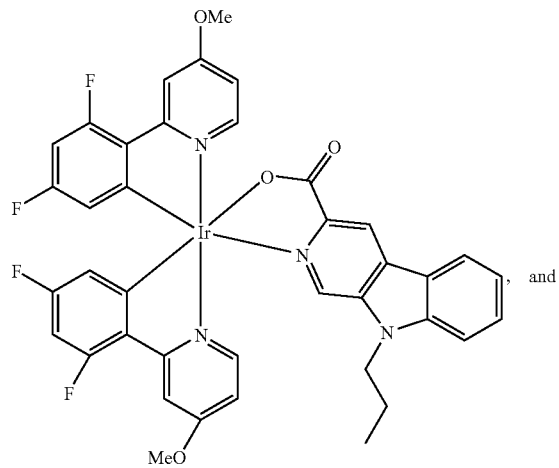
, and
<Formula 9>
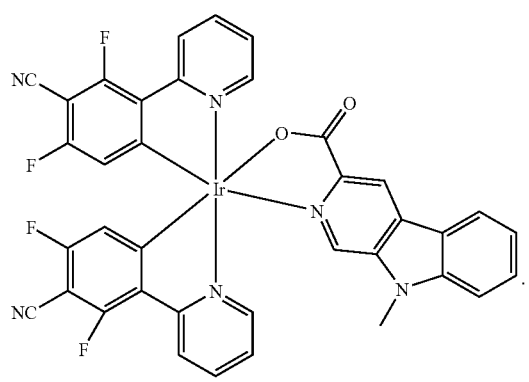
.
3. The organometallic complex of claim 1, wherein the cyclometalating ligand CyN-CyC is one of compounds represented by the following formulae:
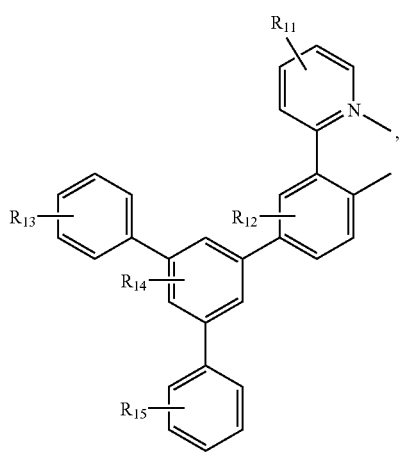
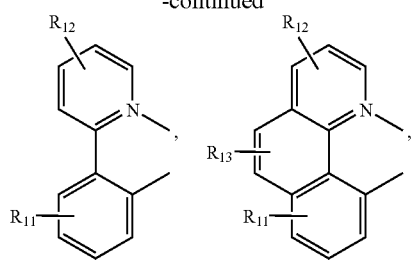
,
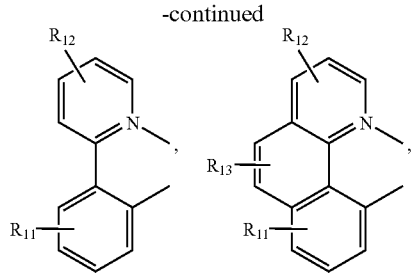
,
-continued
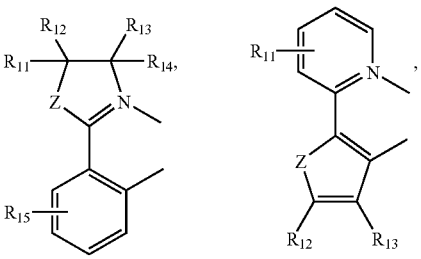
,
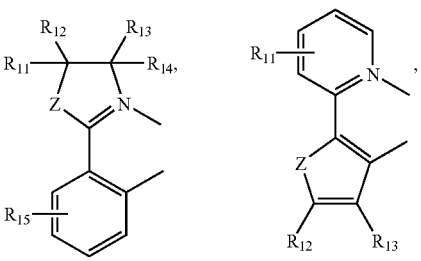

-continued
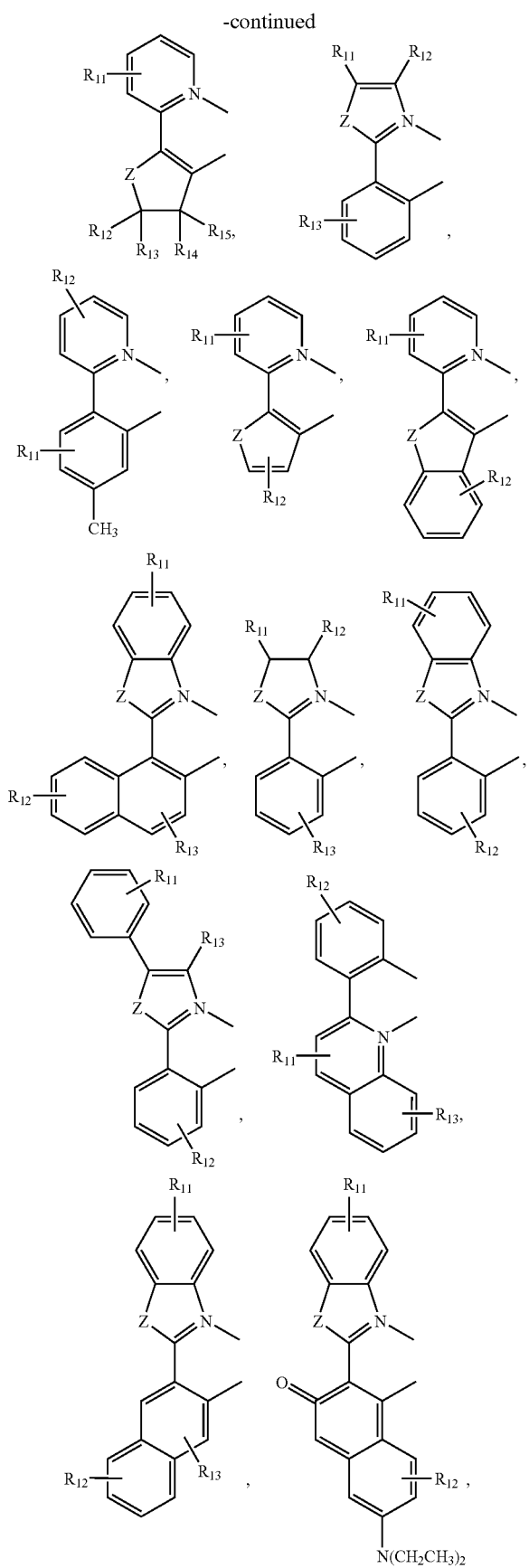
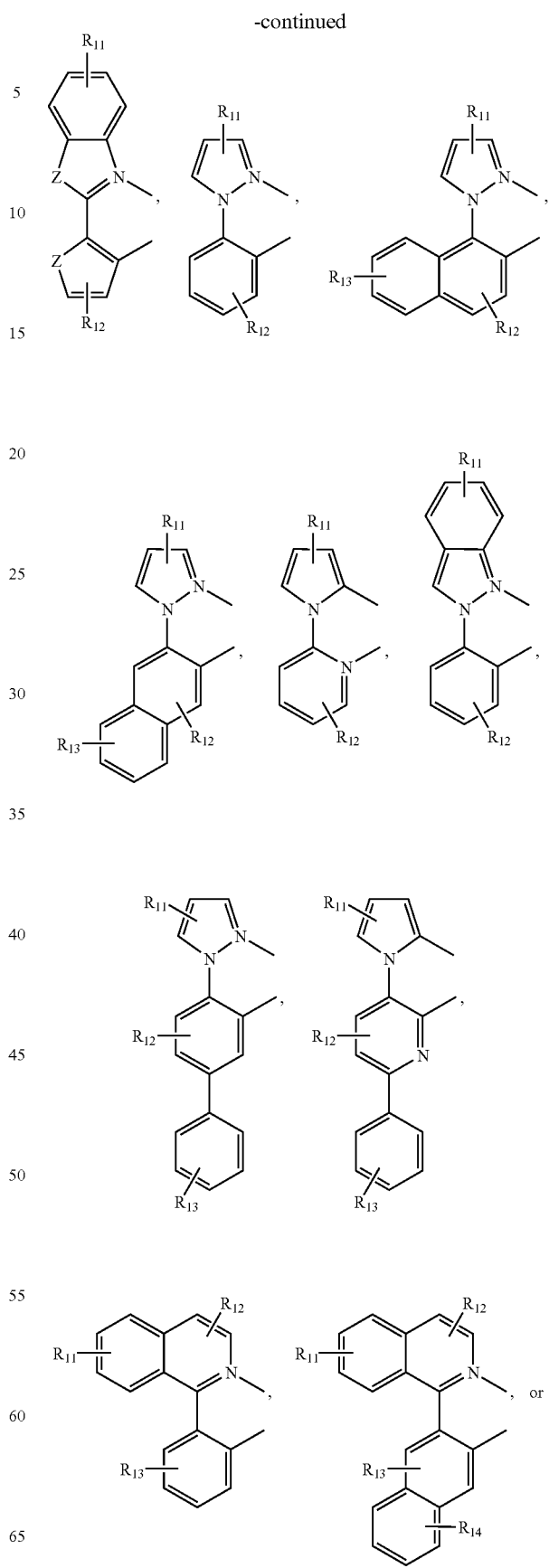

-continued

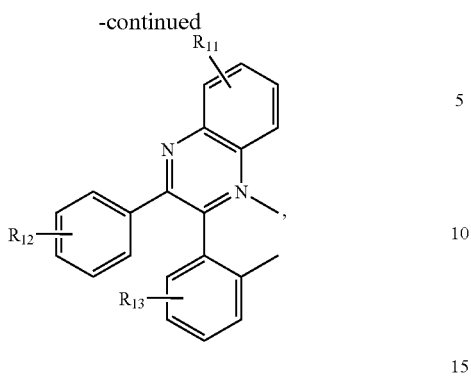

wherein, $R_{11}$, $R_{12}$, $R_{13}$, $R_{14}$, and $R_{15}$ are each independently a monosubstituted or polysubstituted functional group selected from hydrogen, a halogen atom, —OR, —N(R)$_2$, —P(R)$_2$, —POR, —PO$_2$R, —PO$_3$R, —SR, —Si(R)$_3$, —B(R)$_2$, —B(OR)$_2$, —C(O)R, —C(O)OR, —C(O)N(R), —CN, —NO$_2$, —SO$_2$, —SOR, —SO$_2$R, —SO$_3$R, a $C_1$-$C_{20}$ alkyl group, and a $C_6$-$C_{20}$ aryl group where R is selected from hydrogen, a halogen atom, a substituted or unsubstituted $C_1$-$C_{20}$ alkyl group, a substituted or unsubstituted $C_1$-$C_{10}$ alkoxy group, a substituted or unsubstituted $C_2$-$C_{20}$ alkenyl group, a substituted or unsubstituted $C_2$-$C_{20}$ alkynyl group, a substituted or unsubstituted $C_1$-$C_{20}$ heteroalkyl group, a substituted or unsubstituted $C_6$-$C_{40}$ aryl group, a substituted or unsubstituted $C_7$-$C_{40}$ arylalkyl group, a substituted or unsubstituted $C_7$-$C_{40}$ alkylaryl group, a substituted or unsubstituted $C_2$-$C_{40}$ heteroaryl group, and a substituted or unsubstituted $C_3$-$C_{40}$ heteroarylalkyl group; and Z is S, O, or NR$_0$ where R$_0$ is hydrogen or a C1-C20 alkyl group.

4. The organometallic complex of claim 1, wherein the ligand bound to the central metal via nitrogen and oxygen atoms is one of compounds represented by the following formulae:

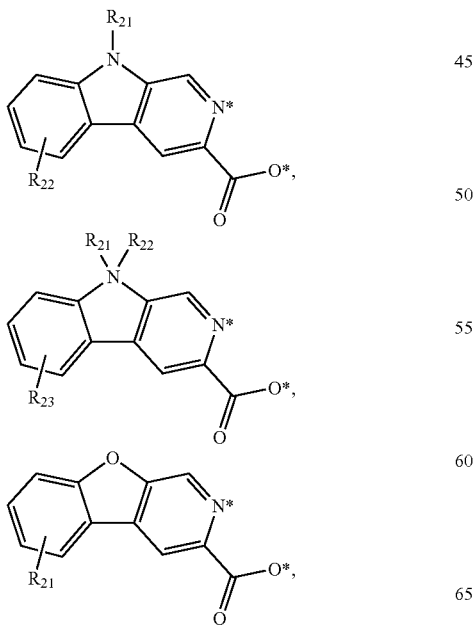

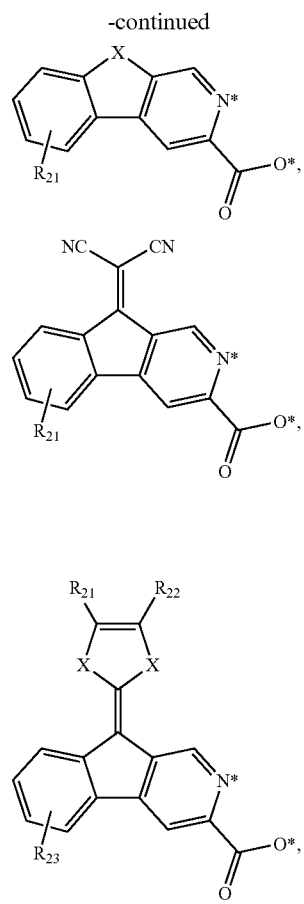

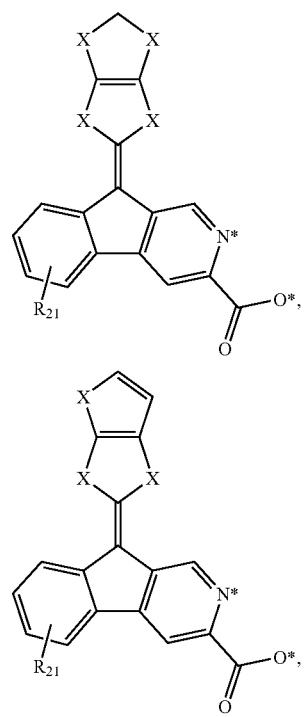

-continued

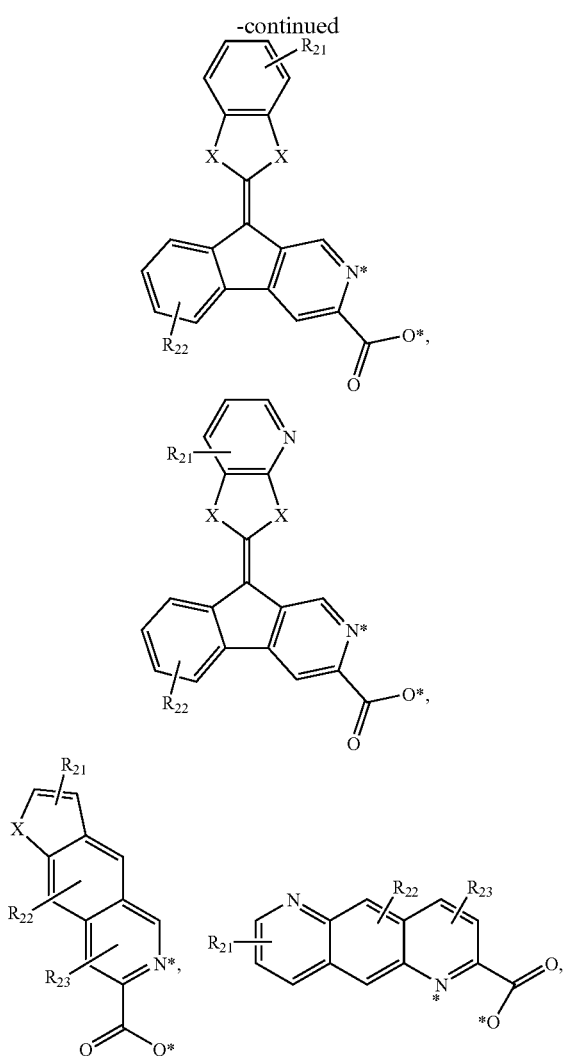

wherein $R_{21}$, $R_{22}$, and $R_{23}$ are each independently a monosubstituted or polysubstituted functional group selected from hydrogen, a halogen atom, —OR, —N(R)$_2$, —P(R)$_2$, —POR, —PO$_2$R, —PO$_3$R, —SR, —Si(R)$_3$, —B(R)$_2$, —B(OR)$_2$, —C(O)R, —C(O)OR, —C(O)N(R), —CN, —NO$_2$, —SO$_2$, —SOR, —SO$_2$R, —SO$_3$R, a $C_1$-$C_{20}$ alkyl group, and a $C_6$-$C_{20}$ aryl group where R is selected from hydrogen, a halogen atom, a substituted or unsubstituted $C_1$-$C_{20}$ alkyl group, a substituted or unsubstituted $C_1$-$C_{10}$ alkoxy group, a substituted or unsubstituted $C_2$-$C_{20}$ alkenyl group, a substituted or unsubstituted $C_2$-$C_{20}$ alkynyl group, a substituted or unsubstituted $C_1$-$C_{20}$ heteroalkyl group, a substituted or unsubstituted $C_6$-$C_{40}$ aryl group, a substituted or unsubstituted $C_7$-$C_{40}$ arylalkyl group, a substituted or unsubstituted $C_7$-$C_{40}$ alkylaryl group, a substituted or unsubstituted $C_2$-$C_{40}$ heteroaryl group, and a substituted or unsubstituted $C_3$-$C_{40}$ heteroarylalkyl group; and X is oxygen or sulfur.

5. The organometallic complex of claim 1, wherein M is Ir or Pt.

6. An organic electroluminescent (EL) device comprising an organic layer interposed between a pair of electrodes, wherein the organic layer comprises the organometallic complex of claim 1.

7. The organic EL device of claim 6, wherein the organic layer is an emitting layer.

8. The organic EL device of claim 6, wherein the content of the organometallic complex is 1 to 30 parts by weight based on the total weight (100 parts by weight) of an emitting layer forming material.

* * * * *